United States Patent [19]

Thomas et al.

[11] Patent Number: 6,022,855
[45] Date of Patent: *Feb. 8, 2000

[54] METHODS AND REAGENTS FOR INHIBITING FURIN ENDOPROTEASE

[75] Inventors: Gary Thomas, Tualatin; Eric D. Anderson, Portland; Laurel Thomas, Tualatin, all of Oreg.; Joel S. Hayflick, Seattle, Wash.

[73] Assignee: Oregan Health Sciences University, Portland, Oreg.

[ * ] Notice: This patent is subject to a terminal disclaimer.

[21] Appl. No.: 08/481,534

[22] PCT Filed: Jan. 7, 1994

[86] PCT No.: PCT/US94/00247

§ 371 Date: Sep. 14, 1995

§ 102(e) Date: Sep. 14, 1995

[87] PCT Pub. No.: WO94/16073

PCT Pub. Date: Jul. 21, 1994

Related U.S. Application Data

[63] Continuation-in-part of application No. 08/002,202, Jan. 8, 1993, Pat. No. 5,604,201.

[51] Int. Cl.[7] .............................. C07K 14/81; C07K 4/12; C07K 5/10; A61K 38/55
[52] U.S. Cl. ............................. 514/12; 530/350; 530/330
[58] Field of Search .................................. 530/350, 300, 530/324, 325, 326–330; 514/12

[56] References Cited

U.S. PATENT DOCUMENTS

| | | | |
|---|---|---|---|
| 4,732,973 | 3/1988 | Barr et al. | 530/350 |
| 5,604,201 | 2/1997 | Thomas et al. | 514/12 |

OTHER PUBLICATIONS

Oda, K. et al. "Proteolytic cleavages of proalbumin and complement pro–C3 in vitro by a truncated soluble form of furin, a mammalian homologue of the yeast Kex2 protease" Biochemical and Biophysical Research Communications (Dec. 30, 1992), vol. 189, No. 3.

George, P.M. et al. "Characterization of antithrombins produced by active site mutagenesis of human alpha 1–antitrypsin expressed in yeast" Blood (Feb. 1989), vol. 73, No. 2, pp. 490–496.

Molloy, S.S. et al. "Human furin is a calcium–dependent serine endoprotease that recognizes the sequence Arg–X–X––Arg and efficiently cleaves anthrax toxin protective antigen" Journal of Biological Chemistry (Aug. 1992), vol. 267, No. 23, pp. 16396–16402.

Klimpel, K.R. et al. "Cleavage of diptheria toxin and the protective antigen of *Bacillus–anthracis* by the eukaryotic endoprotease furin" Abstracts of the General Meeting of the American Society for Microbiology (May, 1992), vol. 92, p. 31.

*Primary Examiner*—Robert A. Wax
*Assistant Examiner*—Kawai Lau
*Attorney, Agent, or Firm*—McDonnell Boehnen Hulbert & Berghoff

[57] ABSTRACT

This invention relates to method and reagents for inhibiting furin endoprotease activity and specifically for inhibiting furin endoprotease-mediated maturation of bioactive proteins in vivo and in vitro. The invention specifically provides proteins capable of inhibiting furin endoprotease activity. Particularly provided are $\alpha_1$-antitrypsin variants that specifically inhibit furin endoprotease activity. Methods for using furin endoprotease inhibition to attenuate or prevent viral protein maturation, and thereby alleviate viral infections, are provided. Also provided are methods for using furin endoprotease inhibition to attenuate or prevent proteolytic processing of bacterial toxins, thereby alleviating bacterial infections. Methods are also provided to inhibit proteolytic processing of biologically active proteins and peptides. The invention also provides pharmaceutically acceptable compositions of therapeutically effective amounts of furin endoprotease inhibitors.

18 Claims, 10 Drawing Sheets

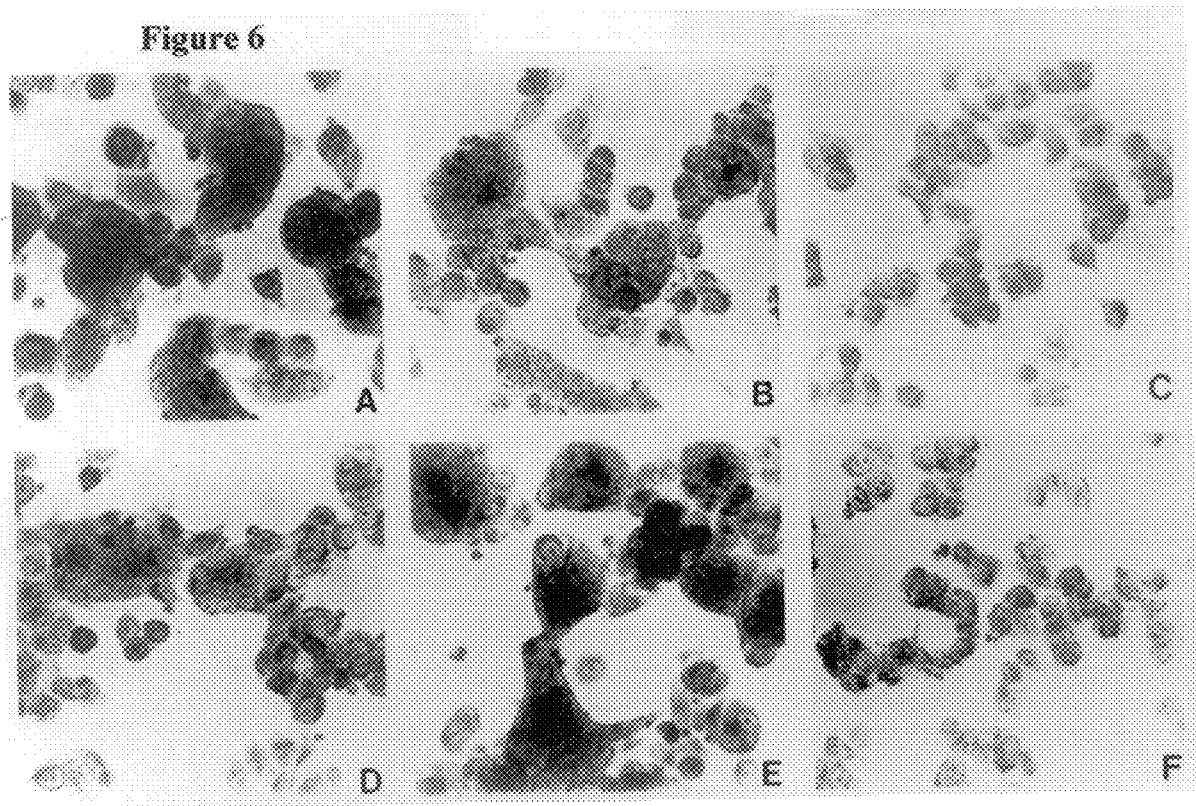

METHODS AND REAGENTS FOR INHIBITING FURIN ENDOPROTEASE

This application is a continuation-in-part of Ser. No. 08/002,202 file Jan. 8, 1993, now U.S. Pat. No. 5,604,201.

This invention was made with government support under DK44629 and DK37274 from the National Institutes of Health. The government has certain rights in the invention.

BACKGROUND OF THE INVENTION

1. Field of the Invention

This invention relates to endoproteases, particularly a novel endoprotease termed furin endoprotease. The invention also relates to inhibitors of furin endoprotease activity. In particular, the invention relates to novel variants of $\alpha_1$-antitrypsin that specifically inhibit furin endoprotease activity. The invention also provides methods for using such inhibitors to attenuate or prevent biological proteolytic maturation of bioactive proteins and peptides in vivo and in vitro, in particular viral proteins and bacterial toxins. Therapeutic methods and pharmaceutical compositions of such inhibitors are also provided directed towards the alleviation and treatment of disease having microbiological etiology.

2. Background of the Related Art

Most biologically active peptides and proteins are synthesized initially as larger, inactive precursor proteins that are endoproteolytically cleaved during transit through the secretory pathway in the Golgi apparatus in cells expression such proteins (see Barr, 1991, Cell 66: 1–3 for review). This system comprises an important common mechanism required for synthesis of biologically active proteins and peptides in yeast (Fuller et al., 1988, Ann. Rev. Physiol. 50: 345–362), invertebrates (Scheller et al., 1983, Cell 32: 7–22) and mammalian cells (Sossin et al., 1989, Neuron 2: 1407–1417). Examples of proteins produced in vivo by exocytotic transport through the Golgi are precursors of peptide hormones, neuropeptides, growth factors, coagulation factors, serum albumin, cell surface receptors, and adhesion molecules.

Morrison et al., 1985, J. Virol. 53: 851–857 disclose that F protein of Newcastle disease virus is processed through the exocytotic transport pathway in infected cells.

Perez & Hunter, 1987, J. Virol. 61: 1609–1614 disclose that the Rous sarcoma virus (RSV) glycoprotein is processed through the exocytotic transport pathway in infected cells.

Yamada et al., 1988, Virology 165: 268–273 disclose that F protein of mumps virus is processed through the exocytotic transport pathway in infected cells.

Randolph et al., 1990, Virology 174: 450–458 disclose that the prM protein of flaviviruses is processed through the exocytotic transport pathway in infected cells.

A common structural feature of molecules processed through the exocytotic transport pathway is the presence of basic residues or pairs of basic residues at the proteolytic processing site in the molecule. Examples include serum factors (Factor IX; Bentley et al., 1987, Cell 45: 343–348; proalbumin; Knowles et al., 1980, Science 209: 497–499; pro-von Willibrand factor; Bonthron et al., 1986, Nature 324: 270–273), viral polyproteins (human immunodeficiency virus (HIV) gp160; McCune et al., 1988, Cell 53: 55–67; RSV envelope protein; Perez & Hunter, 1987, J. Virol. 61: 1609–1614; yellow fever virus protein; Rice et al., 1985, Science 229: 726–733; measles virus protein; Richardson et al., 1986, Virology 155: 508–523; mumps virus protein; Waxham et al., 1987, Virology 159: 381–389; human cytomegalovirus protein; Spaete et al., 1990, J. Virol. 64: 2922–2931; varicella zooster virus protein; Keller et al., 1986, Virology 152: 181–191), growth factors (preprotransforming growth factor β; Gentry et al., 1988, Molec. Cell. Biol. 8: 4162–4168; epidermal growth factor; Gray et al., 1983, Nature 303: 722–725; pro-β-nerve growth factor (NGF); Edwards et al., 1988, Molec. Cell Biol. 8: 2456–2464), receptors (insulin receptor; Yoshimasa et al., 1988, Science 240: 784–787); and bacterial toxins (see Stephen & Pietrowski, 1986, *Bacterial Toxins,* 2d ed. (Amer. Soc. Microbiol. Washington, D.C.) for review; anthrax toxin; Singh et al., 1989, J. Biol. Chem. 264: 11099–11102). The proteolytic processing site has been identified in some of these molecules.

Berger & Shooter, 1977, Proc. Natl. Acad. Sci. USA 74: 3647–3651 disclose the sequence -RSKR- (SEQ ID NO.: 1) at the proteolytic processing site of pro-β-NGF.

Bentley et al., 1986, ibid. disclose the sequence -RPKR- (SEQ ID NO.: 2) at the proteolytic processing site of the blood coagulation factor protein Factor IX.

McCune et al., 1988, ibid., disclose the sequence -REKR- (SEQ ID NO.: 3) at the proteolytic processing site of HIV gp160.

Clepak et al., 1988, Biochem. Biophys. Res. Comm. 157: 747–754 disclose the sequence -RVRR- (SEQ ID NO.: 4) at the proteolytic processing site of diphtheria toxin.

Vey et al., 1992, Virology 188: 408–413 disclose the sequence -RX(R/K)R- (SEQ ID NO.: 5) at the proteolytic processing site of influenza hemagglutinin.

Ogata et al., 1990, J. Biol. Chem. 265: 20678–20685 disclose the sequence -RSKR- (SEQ ID NO.: 1) at the proteolytic processing site of Pseudomonas exotoxin A.

Klimpel et al., 1992, Proc. Natl. Acad. Sci. USA 89: 10277–10281 disclose the sequence -RX(R/K)R- (SEQ ID NO.: 5) at the proteolytic processing site of anthrax protective antigen.

Recently, an endoprotease termed furin has been isolated that specifically recognizes the recognition sequence of proteins processed through the exocytotic secretory pathway (Wise et al., 1990, Proc. Natl. Acad. Sci. USA 87: 9378–9382; Bresnahan et al., 1990, J. Cell Biol. 111: 2851–2859). This endoprotease is a subtilisin-related, calcium-dependent serine protein (Bresnahan et al., ibid.). A complementary DNA copy of the mRNA encoding this endoprotease has been isolated (Wise et al., ibid.) and sequenced (van den Ouweland et al., 1992, Nucleic Acids Res. 18: 664) and expressed in heterologous cells (Bresnahan et al., ibid.). These studies have shown furin to be expressed as a doublet of 96 and 90 kilodaltons (kD) in size, ubiquitously expressed as a 4.5 kilobase (kb) mRNA, and localized by fluorescence immunohistochemistry to the Golgi apparatus of cells expressing this endoprotease (Bresnahan et al., ibid.). Furin has been shown to be capable of proteolytically cleaving a number of exocytotically processed proteins.

Bresnahan et al., ibid., disclose furin-mediated cleavage of pro-β-NGF.

Wise et al., ibid., disclose furin-mediated cleavage of pro-von Willibrand factor and complement factor C3.

Hosaka et al., 1991, J. Biol. Chem. 266: 12127–12130 disclose furin-mediated cleavage of renin.

Steineke-Grober et al., 1992, EMBO J. 11: 2407–2414 disclose furin-mediated cleavage of influenza hemagglutinin.

Klimpel et al., 1992, Proc. Natl. Acad. Sci. USA 89: 10277–10281 disclose furin-mediated cleavage of anthrax protective antigen.

Molloy et al., 1992, J. Biol. Chem 267: 16396–16402 disclose furin-mediated cleavage of anthrax protective antigen.

Klimpel et al., 1992, Annual Meeting, Amer. Soc. Microbiol. Abst. B-32 disclose furin-mediated cleavage of diphtheria toxin.

Furin can be inhibited by specific peptidyl chloroalkylketones (Garten et al., 1989, Virology 172: 25–31; Molloy et al., ibid.; Hallenberger et al., 1992, Nature 360: 358–361), but these substances are toxic in vivo. Given the importance of the endoprotease in activation of bacterial toxins, viral structural proteins and bioactive molecules, there is a need for the development of safe and specific furin inhibitors.

SUMMARY OF THE INVENTION

This invention provides safe, specific and effective inhibitors of furin endoprotease that are novel variants of the naturally-occurring protease inhibitor, $\alpha_1$-antitrypsin (SEQ ID NO.: 6) (Heeb et al., 1990, J. Biol. Chem 265: 2365–2369; Schapira et al., 1987, J. Clin. Invest. 80: 582–585) and peptides derived therefrom. Use of these novel variants of $\alpha_1$-antitrypsin is advantageous because $\alpha_1$-antitrypsin and variants are secreted proteins that are processed by the exocytotic secretory pathway through the Golgi, so synthesis of these proteins in a cell would result in delivery of the inhibitor to the site of furin activity in vivo.

In a first embodiment, the invention provides a furin endoprotease inhibitor comprising an $\alpha_1$-antitrypsin variant protein having an amino acid sequence comprising the amino acids of the native $\alpha_1$-antitrypsin molecule (disclosed in Long et al., 1984, Biochemistry 23: 4828–4837, incorporated by reference), except that the sequence at position 355–358 of the native protein (-Ala-Ile-Pro-Met-) (SEQ ID NO.: 7) is changed to the novel sequence -Arg-Xaa-Xaa-Arg- (SEQ ID NO.: 8), wherein each Xaa is any amino acid, at positions 355–358 of the native $\alpha_1$-antitrypsin amino acid sequence. In a preferred embodiment, the $\alpha_1$-antitrypsin variant is $\alpha_1$-antitrypsin Portland (SEQ ID NO.: 9) and the amino acid sequence at positions 355–358 of the $\alpha_1$-antitrypsin amino acid Portland and the amino acid sequence is -Arg-Ile-Pro-Arg- (SEQ ID NO.: 10).

In a second embodiment, the invention provides a nucleic acid having a nucleotide sequence that encodes an $\alpha_1$-antitrypsin variant protein having an amino acid sequence comprising the amino acids of the native $\alpha_1$-antitrypsin molecule, except that the sequence at position 355–358 of the native protein (-Ala-Ile-Pro-Met-) (SEQ ID NO.: 7) is changed to the novel sequence -Arg-Xaa-Xaa-Arg- (SEQ ID NO.: 8), wherein each Xaa is any amino acid, at positions 355–358 in the variant $\alpha_1$-antitrypsin amino acid sequence. In a preferred embodiment, the $\alpha_1$-antitrypsin variant is $\alpha_1$-antitrypsin Portland and the amino acid sequence is -Arg-Ile-Pro-Arg- (SEQ ID NO.: 10).

In a third embodiment, the invention provides a recombinant expression construct comprising a nucleic acid having a nucleotide sequence encoding an $\alpha_1$-antitrypsin variant protein with an amino acid sequence comprising the amino acids of the native $\alpha_1$-antitrypsin molecule, except that the sequence at position 355–358 of the native protein (-Ala-Ile-Pro-Met-) (SEQ ID NO.: 7) is changed to the novel sequence -Arg-Xaa-Xaa-Arg- (SEQ ID NO.: 8), wherein each Xaa is any amino acid, at positions 355–358 of the variant $\alpha_1$-antitrypsin amino acid sequence. In a preferred embodiment, the $\alpha_1$-antitrypsin variant is $\alpha_1$-antitrypsin Portland and the amino acid sequence is -Arg-Ile-Pro-Arg- (SEQ ID NO.: 10). The recombinant expression construct provided by the invention is capable of expression $\alpha_1$-antitrypsin variant proteins of the invention in a culture of transformed cells. In a preferred embodiment, the recombinant expression construct comprises a vaccinia virus-based construct. In a more preferred embodiment, the recombinant expression construct comprises a recombinant vaccinia virus vector covalently linked to the nucleic acid encoding the $\alpha_1$-antitrypsin variant, preferably $\alpha_1$-antitrypsin Portland.

The invention also provides a cell culture transformed with the recombinant expression construct encoding an $\alpha_1$-antitrypsin variant capable of expressing the $\alpha_1$-antitrypsin variant. In a preferred embodiment, the $\alpha_1$-antitrypsin variant is $\alpha_1$-antitrypsin Portland. Preferred embodiments of such cell cultures of bacterial cells, yeast cells, insect cells or mammalian cells.

In another embodiment, the invention provides a homogenous composition of matter comprising an $\alpha_1$-antitrypsin variant produced by the cell culture according to the teachings of the invention. In a preferred embodiment, the $\alpha_1$-antitrypsin variant is $\alpha_1$-antitrypsin Portland.

The invention also provides a furin endoprotease inhibitor comprising $\alpha_1$-antitrypsin variants capable of blocking endoproteolytic activation of bacterial toxins. In a preferred embodiment, the $\alpha_1$-antitrypsin variant is $\alpha_1$-antitrypsin Portland. Pharmaceutically acceptable compositions of the $\alpha_1$-antitrypsin variants of the invention are also provided comprising a therapeutically effective amount of $\alpha_1$-antitrypsin variant and a pharmaceutically acceptable carrier or diluent.

Also provided by the invention are peptides having an amino acid sequence of about 4 to about 100 amino acids in length, comprising the amino acid sequence -Arg-Xaa-Xaa-Arg-, wherein each Xaa is any amino acid. In a preferred embodiment, the amino acid sequence is -Arg-Ile-Pro-Arg-.

The invention provides a method of inhibiting bacterial infection of human cells comprising contacting such cells with an $\alpha_1$-antitrypsin variant of the invention. In a preferred embodiment, the $\alpha_1$-antitrypsin variant is $\alpha_1$-antitrypsin Portland. In a preferred embodiment, the bacterial infection is caused by *Corynebacterium diptheriae*. In another preferred embodiment, the bacterial infection is caused by *Bacillus anthracis*. In yet another preferred embodiment, the bacterial infection is caused by *Pseudomonas aeruginosa*.

The invention also provides a method of inhibiting bacterial infection in a human comprising administering a therapeutically effective amount of an $\alpha_1$-antitrypsin variant of the invention in a pharmaceutically acceptable carrier. In a preferred embodiment, the $\alpha_1$-antitrypsin variant is $\alpha_1$-antitrypsin Portland. In a preferred embodiment, the bacterial infection is caused by *Corynebacterium diptheriae*. In another preferred embodiment, the bacterial infection is caused by *Bacillus anthracis*. In yet another preferred embodiment, the bacterial infection is caused by *Pseudomonas aeruginosa*.

The invention provides a method of treating humans with a bacterial infection comprising administering a therapeutically effective amount of an $\alpha_1$-antitrypsin variant of the invention in a pharmaceutically acceptable carrier. In a preferred embodiment, the $\alpha_1$-antitrypsin variant is $\alpha_1$-antitrypsin Portland. In a preferred embodiment, the bacterial infection is caused by *Corynebacterium diptheriae*. In another preferred embodiment, the bacterial infection is caused by *Bacillus anthracis*. In yet another preferred embodiment, the bacterial infection is caused by *Pseudomonas aeruginosa*.

Another method provided by the invention for treating humans with a bacterial infection comprises administering a combination of therapeutically effective amount of an $\alpha_1$-antitrypsin variant and a therapeutically effective amount of a second antibacterial compound in a pharmaceutically acceptable carrier. In a preferred embodiment, the $\alpha_1$-antitrypsin variant is $\alpha_1$-antitrypsin Portland. In a preferred embodiment, the bacterial infection is caused by *Corynebacterium diptheriae*. In another preferred embodiment, the bacterial infection is caused by *Bacillus anthracis*. In yet another preferred embodiment, the bacterial infection is caused by *Pseudomonas aeruginosa*.

Pharmaceutically acceptable compositions effective according to the methods of the invention, comprising a therapeutically effective amount of a furin endoprotease inhibitor capable of blocking endoproteolytic activation of bacterial toxins and a pharmaceutically acceptable carrier or diluent, are also provided.

The invention provides a method of inhibiting viral infection of human cells comprising contacting such cells with an $\alpha_1$-antitrypsin variant according to the invention. In a preferred embodiment, the invention provides a gene therapy delivery system for a nucleic acid encoding an $\alpha_1$-antitrypsin variant comprising the recombinant expression construct of the invention and genetic means for delivery and expression of the recombinant expression construct into the cells of an animal. A preferred $\alpha_1$-antitrypsin variant is $\alpha_1$-antitrypsin Portland. Pharmaceutically acceptable compositions comprising a therapeutically effective amount of the gene therapy delivery system and a pharmaceutically acceptable carrier or diluent are provided by the invention. In a preferred embodiment, the viral infection is caused by Human Immunodeficiency Virus 1 (HIV-1). In another preferred embodiment, the human cells are hematopoietic cells, most preferably T lymphocytes. Other preferred embodiments of viral infections include infection by influenza virus.

The invention also provides a method for inhibiting a viral infection in an animal, most preferably a human, comprising administering a therapeutically effective amount of the gene therapy delivery system of the invention in a pharmaceutically acceptable carrier. In a preferred embodiment, the virus is Human Immunodeficiency Virus 1 (HIV-1). In another preferred embodiment, the virus is cytomegalovirus.

The invention provides a method of treating humans infected with a virus comprising administering a therapeutically effective amount of the gene therapy delivery system of the invention in a pharmaceutically acceptable carrier. In a preferred embodiment, the virus is Human Immunodeficiency Virus 1 (HIV-1). In another preferred embodiment, the virus is influenza virus.

The invention provides a method of treating humans infected with a virus comprising administering a combination of a therapeutically effective amount of the gene therapy delivery system of the invention and a therapeutically effective amount of a second antiviral compound in a pharmaceutically acceptable carrier. In a preferred embodiment, the virus is Human Immunodeficiency Virus 1 (HIV-1) and the second antiviral compound is azidothymidine. In another preferred embodiment, the virus is influenza virus.

The invention also provides a method for treating virus-associated immunosuppression in a human comprising administering a therapeutically effective amount of the gene therapy delivery system of the invention in a pharmaceutically acceptable carrier. In a preferred embodiment, the virus is Human Immunodeficiency Virus 1(HIV-1).

Pharmaceutically acceptable compositions effective according to the methods of the invention, comprising a therapeutically effective amount of the gene therapy delivery system encoding $\alpha_1$-antitrypsin variants having antiviral properties and a pharmaceutically acceptable carrier or diluent, are also provided. In a preferred embodiment, the $\alpha_1$-antitrypsin variant is $\alpha_1$-antitrypsin Portland.

The invention also provides a method of inhibiting proteolytic processing of a biologically active protein or peptide in a cell comprising contacting such cells with the gene therapy delivery system of the invention. Preferred biologically active proteins are pro-$\beta$-nerve growth factor, blood coagulation factor protein Factor IX, pro-von Willibrand factor, complement factor C3 and renin.

BRIEF DESCRIPTION OF THE DRAWINGS

FIGS. 6A through 6F illustrates the results of the syncytium experiments described in Example 5.

DETAILED DESCRIPTION OF THE PREFERRED EMBODIMENTS

Figure 1:
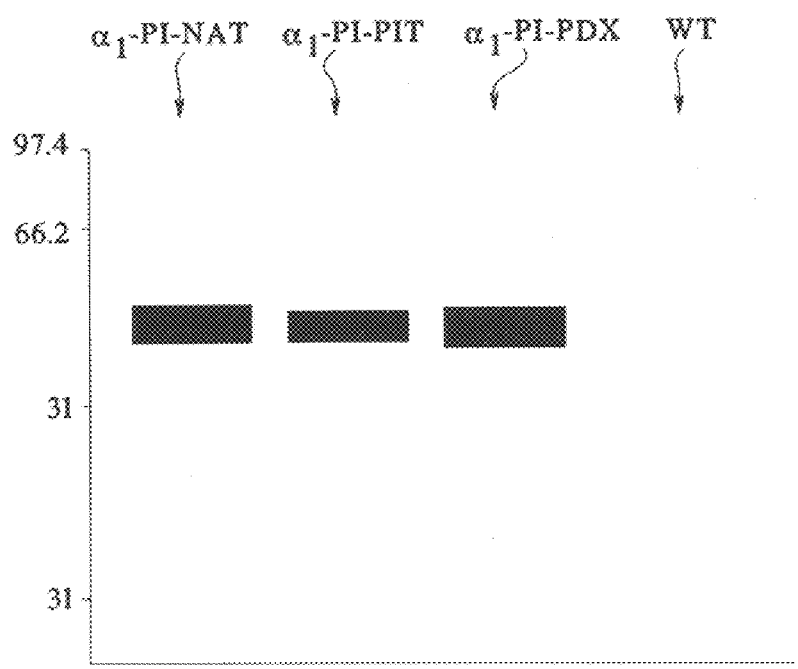
FIG. 1 illustrates production of native $\alpha_1$-antitrypsin (Lane 1), $\alpha_1$-antitrypsin Pittsburgh (Lane 2) and $\alpha_1$-antitrypsin Portland (Lane 3) by BSC-40 cells infected with vaccinia virus recombinant constructs.
Figure 2:
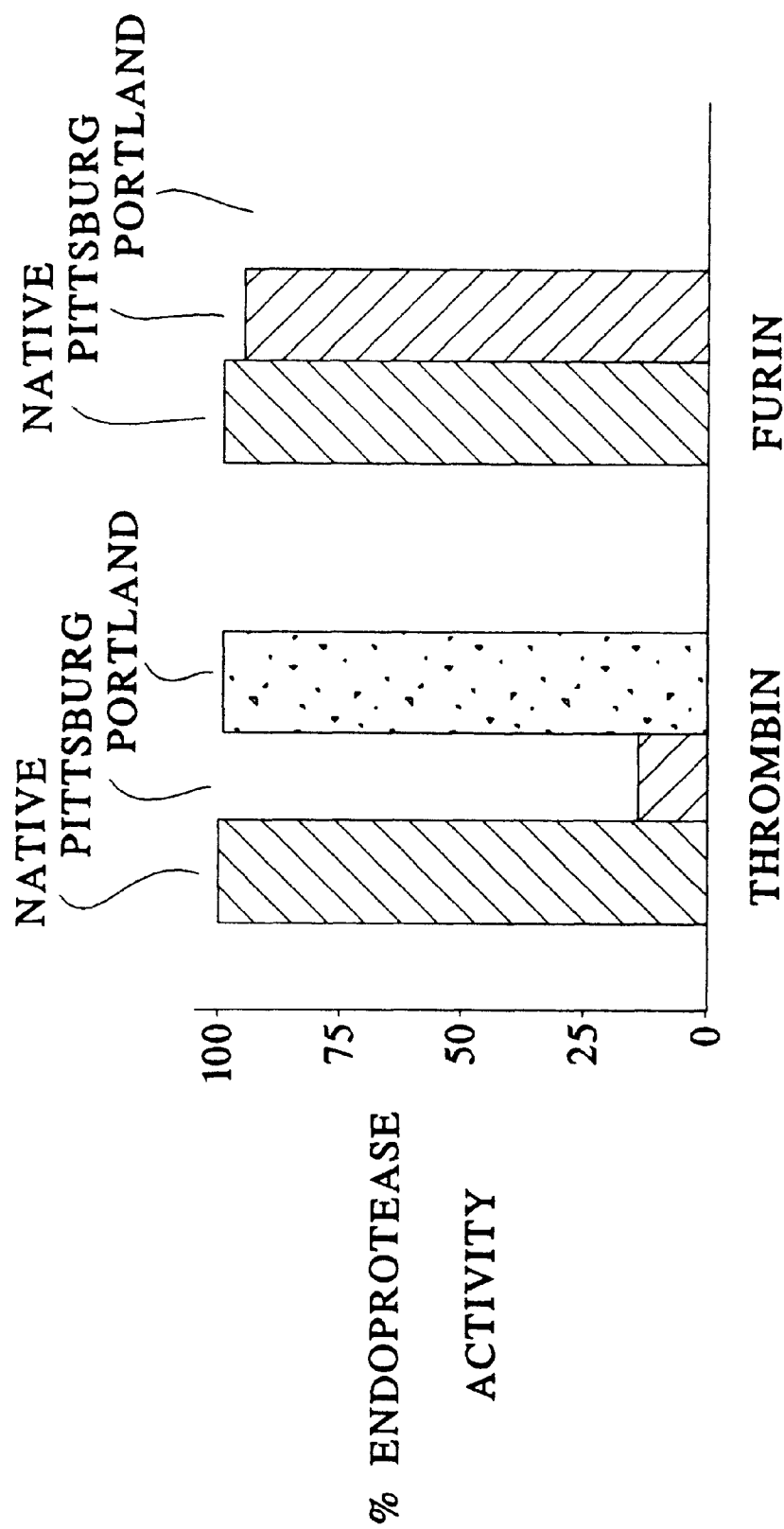
FIG. 2 shows inhibition of thrombin and furin by native $\alpha_1$-antitrypsin (striped bars), $\alpha_1$-antitrypsin Pittsburgh (dotted bars) and $\alpha_1$-antitrypsin Portland (stipled bars) in vitro.

The production of proteins such as the $\alpha_1$-antitrypsin Portland from cloned genes by genetic engineering is well known. See, e.g., U.S. Pat. No. 4,761,371 to Bell et al. at Col. 6 line 3 to Col. 9 line 65. (The disclosure of all U.S. patent references cited herein is to be incorporated herein by reference.) The discussion which follows is accordingly intended as an overview of this field, and is not intended to reflect the full state of the art. For the purposes of this discussion, the $\alpha_1$-antitrypsin variant $\alpha_1$-antitrypsin Portland will be used as an exemplar; it will be understood that the discussion applies to and the invention encompasses all the $\alpha_1$-antitrypsin variants of the invention.

DNA which encodes $\alpha_1$-antitrypsin Portland may be obtained, in view of the instant disclosure, by chemical synthesis, or by in vitro mutagenesis as described in Example 2 herein of the native $\alpha_1$-antitrypsin DNA sequence. Such native $\alpha_1$-antitrypsin DNA can be obtained by screening reverse transcripts of mRNA from appropriate cells or cultured cell lines, by screening genomic libraries from appropriate cells, or by combinations of these procedures. Screening of mRNA or genomic DNA may be carried out with probes generated from the known $\alpha_1$-antitrypsin gene sequence. Probes may be labeled with a detectable group such as a fluorescent group, a radioactive atom or a chemiluminescent group in accordance with know procedures and used in conventional hybridization assays (see Sambrook et al., 1990, *Molecular Cloning: A Laboratory Manual*, Cold Spring Harbor Laboratory Press, N.Y.). In the alternative, $\alpha_1$-antitrypsin gene sequences may be obtained for in vitro mutagenesis by use of the polymerase chain reaction (PCR) procedure, with the PCR oligonucleotide primers being produced from the native $\alpha_1$-antitrypsin gene sequence. See U.S. Pat. Nos. 4,683,195 to Mullis et al. and 4,683,202 to Mullis.

$\alpha_1$-antitrypsin variants such as $\alpha_1$-antitrypsin Portland may be synthesized in host cells transformed with a recombinant expression construct comprising a DNA sequence encoding an $\alpha_1$-antitrypsin variant. Such a recombinant expression construct can also be comprised of a vector that is a replicable DNA construct. Vectors are used herein either to amplify DNA encoding $\alpha_1$-antitrypsin Portland and/or to express DNA encoding $\alpha_1$-antitrypsin Portland. For the purposes of this invention, a recombinant expression construct is a replicable DNA construct in which a DNA sequence encoding an $\alpha_1$-antitrypsin variant is operably linked to suitable control sequences capable of effecting the expression of the $\alpha_1$-antitrypsin variant in a suitable host. The need for such control sequences will vary depending upon the host selected and the transformation method chosen. Generally, control sequences include a transcriptional promoter, an optional operator sequence (in bacteria) or enhancer sequence (in eukaryotic cells) to control transcription, a sequence encoding suitable mRNA ribosomal binding sites, and sequences which control the termination of transcription and translation. Amplification vectors do not require expression control domains. All that is needed is the ability to replicate in a host, usually conferred by an origin of replication, and a selection gene to facilitate recognition of transformants.

DNA regions are operably linked when they are functionally related to each other. For example: a promoter is operably linked to a coding sequence if it controls the transcription of the sequence; a ribosome binding site is operably linked to a coding sequence if it is positioned so as to permit translation. Generally, operably linked means contiguous and, in the case of leaders sequences, contiguous and in the same translational reading frame.

Vectors useful for practicing the present invention include plasmids, viruses (including phage), retroviruses, and integratable DNA fragments (i.e., fragments integratable into the host genome by homologous recombination). The vector may replicate and function independently of the host genome, or may, in some instances, integrate into the genome itself. Suitable vectors will contain replicon and control sequences which are derived from species compatible with the intended expression host. A preferred vector is the plasmid pZVneo, useful for producing recombinant expression constructs based on homologous recombination with vaccinia virus sequences.

A preferred embodiment of the recombinant expression constructs of this invention comprise vaccinia virus sequences capable of infecting mammalian cells and an expressing $\alpha_1$-antitrypsin variant, as described below in Example 2.

Transformed host cells are cells which have been transformed or transfected with a recombinant expression construct made using recombinant DNA techniques and comprising sequences encoding an $\alpha_1$-antitrypsin variant. Transformed host cells may express $\alpha_1$-antitrypsin Portland, but host cells transformed for purposes of cloning or amplifying DNA need not express these sequences.

Cultures of cells, including cells derived from multicellular organisms, are desirable hosts for recombinant $\alpha_1$-antitrypsin Portland synthesis. In principal, any cell culture is useful that is capable of being transformed with an appropriate recombinant expression construct and expression $\alpha_1$-antitrypsin protein. The invention is preferably practiced with bacterial, yeast, insect or mammalian cells, however, mammalian cells are more preferred, as illustrated in the Examples. Propagation of bacteria and yeast is well known in the art, and propagation of mammalian cells in cell culture has become a routine procedure. See *Tissue Culture*, Academic Press, Kruse & Patterson, editors (1973). Most preferred mammalian cells are BSC-40 African green monkey kidney cells, but other cells, such as human 293 cells, VERO and HeLa cells, Chinese hamster ovary (CHO) cell lines, and WI138, BHK, COS-7, CV, and MDCK cells, are also useful.

The invention provides homogeneous compositions of $\alpha_1$-antitrypsin Portland produced by transformed cells as provided herein. Such homogeneous compositions are intended to be comprised of mammalian $\alpha_1$-antitrypsin Portland protein that comprises at least 90% of the protein in such homogenous composition.

The recombinant expression constructs of the present invention are useful in molecular biology to transform cells in vivo in an animal as a method for protecting the animal from viral or other infection in cells that express furin or a furin-like endoprotease activity that can be inhibited by $\alpha_1$-antitrypsin Portland. The invention provides a gene therapy delivery system comprising the recombinant expression constructs of the invention in a configuration that enables safe and efficient introduction of these sequences into appropriate cells and expression of $\alpha_1$-antitrypsin Portland. For such purposes, retroviral vectors as described in U.S. Pat. No. 4,650,764 to Temin & Watanabe or U.S. Pat. No. 4,861,719 to Miller may be employed, for example. The recombinant expression constructs of the invention may also be used in gene therapy carried out using homologous recombination. See generally Thomas & Capecchi, 1987, Cell 51: 503–512; Bertling, 1987, Bioscience Reports 7: 107–112; Smithies et al., 1985, Nature 317: 230–234. Additionally, alteration of endogenous $\alpha_1$-antitrypsin sequences to produce $\alpha_1$-antitrypsin Portland in cells carrying such altered $\alpha_1$-antitrypsin sequences can also be achieved using homologous recombination or other techniques. Transgenic animals, the tissues of which express the $\alpha_1$-antitrypsin Portland variant, are also envisioned as additional objects of this invention.

The peptides of this invention may be generated and/or isolated by any means known in the art. It is within the skill of those of ordinary skill in the art to isolate or chemically synthesize a nucleic acid encoding each of the peptides of the invention. Such nucleic acids are advantageously utilized as components of recombinant expression constructs, wherein the nucleic acids are operably linked with transcriptional and/or translational control elements, whereby the recombinant expression constructs of the invention are capable of expressing the peptides of the invention in cultures of cells, preferably eukaryotic cells, most preferably mammalian cells, transformed with such recombinant expression constructs.

The peptides of the invention may be advantageously synthesized by any of the chemical synthesis techniques known in the art, particularly solid-phase synthesis techniques, for example, using commercially-available automated peptide synthesizers. Such peptides may be provided as linear peptides encompassing the amino acid sequence -Arg-Xaa-Xaa-Arg-, where each Xaa is any amino acid. These peptides may also be provided in the form of combination peptides, wherein the peptides comprising the combination are linked in a linear fashion one to another, with or without separation by "spacer" amino acids allowing for selected conformational presentation. Also provided are branched-chain combinations, wherein the component peptides are covalently linked via functionalities in amino acid sidechains of the amino acids comprising the peptides.

The invention also provides antibacterial and antiviral methods. The invention provides methods for blocking endoproteolytic activation of bacterial toxins. Bacterial targets of the antibacterial methods provided by this invention include but are not limited to any bacteria that produces an endoproteolytically-activated toxin, such as diptheria toxin produced by *Corynebacterium diptheriae,* exotoxin A of *Pseudomonas aeruginosa,* tetanus toxin, the enterotoxins of *Escherichia coli* and *Vibrio cholerae,* protective antigen of *Bacillus anthracis* and the neurotoxin and C2 toxin of *Clostridium botulinum.* Preferred toxins are those that are proteolytically processed at a consensus furin recognition site (-Arg-Xaa-Xaa-Arg↓-) (SEQ ID NO.: 8). Preferred embodiments include *Corynebacterium diptheriae, Pseudomonas aeruginosa* and *Bacillus anthracis.*

Viral targets of antiviral methods provided include but are not limited to picornaviruses (e.g., poliovirus and rhinovirus); orthomyxoviruses (e.g., influenza virus); paramyxoviruses (e.g., measles virus and mumps virus); coronaviruses; rhabdoviruses (e.g., rabies virus and vesicular stomatitis virus); togaviruses (e.g., Semliki Forest virus and yellow fever virus); bunyaviruses (e.g., California encephalitis virus); arenaviruses (e.g., Lassa fever virus); rubella virus; reoviruses (e.g., Colorado tick virus); hepatitis viruses; adenoviruses; herpesviruses (e.g., herpes simplex virus); and oncogenic viruses, including papilloma viruses, RNA tumor viruses, or retroviruses, and lentiviruses (e.g., human immune deficiency virus). The most preferred viruses are the human immunodeficiency viruses (HIV-1 and HIV-2).

Cells intended to be protected by the methods provided by this invention include but are not limited to human, canine, bovine, murine, leoporine, porcine, ovine, simian, feline, hircine, and equine cells. The preferred cells are human cells. More preferred cells are human T lymphocytes (T cells), and the most preferred human T cells are those human T cells expressing the cell surface antigen CD4.

The methods of the present invention may be used to treat donated human blood or plasma to protect transfusion recipients from viral infection from contaminating virus. The methods of the present invention may be used to treat human semen to protect embryos derived from such semen, and mothers bearing such embryos or impregnated with such semen, from contaminating virus. In a preferred embodiment, the contaminating virus is HIV-1.

The present invention provides methods for inhibiting viral infection in a human. The invention also provides for treating a human infected with a virus. Another embodiment of the present invention also includes methods for treating immunosuppression in a human associated with viral infection. Yet another embodiment of the present invention provides a method of prophylaxis for treating a human exposed to infection with a virus, in particular those directly at risk of infection as a result of intimate contact with humans infected with a virus of tissues or bodily fluids contaminated by a virus. The preferred virus of these embodiments of the invention is HIV-1. The invention provides pharmaceutically acceptable compositions effective for use with the methods provided by the invention comprising the peptides of the invention and a pharmaceutically acceptable carrier.

The invention also provides methods for inhibiting proteolytic processing of a biologically active protein or peptide in a cell comprising contacting such cells with the gene therapy delivery system of the invention. The methods of the invention encompass inhibition of proteolytic processing of any biologically active molecule that is proteolytically processed by furin in vivo or in vitro, including but not limited to peptide hormones, neuropeptides, growth factors, coagulation factors, serum albumin, cell surface receptors, and adhesion molecules. Preferred biologically active proteins are pro-β-nerve growth factor, blood coagulation factor protein Factor IX, pro-von Willibrand factor, complement factor C3 and renin, for alleviation of pathological conditions and disease states in an animal, preferably a human, associated with over-expression, over-production or otherwise inappropriate synthesis of such biologically-active proteins.

Preparation of pharmaceutically acceptable compositions provided by the present invention can be prepared using methods well known to those with skill in the art. Any of the common carriers such as sterile saline solution, plasma, etc., can be utilized for preparing the pharmaceutical compositions provided by the invention. Routes of administration include but are not limited to oral (including inhalation into the lungs), intravenous, parenteral, rectal, optical, aural and transdermal. The pharmaceutical compositions of the invention may be administered intravenously in any conventional medium for intravenous injection such as an aqueous saline medium, or in blood plasma medium. Such medium may also contain conventional pharmaceutical adjunct materials such as, for example, pharmaceutically acceptable salts to adjust the osmotic pressure, buffers, preservatives and the like. Among the preferred media are normal saline and plasma.

The following Examples illustrate certain aspects of the above-described method and advantageous results (also disclosed in Anderson et al., 1993, J. Biol. Chem. 268: 24887–24891). The following Examples are shown by way of illustration and not by way of limitation.

EXAMPLE 1

Production of Furin Endoprotease in African Green Monkey Cells In Vitro

Human furin was synthesized for inhibition experiments as described in Bresnahan et al., (1990, J. Cell Biol. 111: 2851–2859) and Molloy et al., (1992, J. Biol. Chem. 267:16396–14402; both hereby incorporated by reference). Briefly, a furin cDNA (van den Ouweland et al., 1992, Nucleic Acids Res. 18: 664) encoding a truncated but functional furin protein was inserted into the multiple cloning site of a vaccinia virus vector (see Hruby et al., 1986, Meth. Enzymol. 124: 295–309) and used to infect BSC-40 African green monkey kidney cells (ATCC Accession No. CCL 26, American Type Culture Collection, Rockville, Md.). The cells were incubated in serum-free defined media for 24 hours and then harvested at 4° C. and disrupted by 20–30 strokes in a Dounde homogenizer (Kontes Glass Co., Vineland, Ohio). The lysate was cleared by low-speed centrifugation (1000 g, 5 min) and the supernatant then subjected to ultracentrifugation at 100,000 g for 1 hr. The pellet was resuspended in 200 $\mu$L of a buffer comprising 10 mM HEPES (N-(2-hydroxyethyl)piperazine-N'-(2-ethanesulfonic acid), Sigma Chemical Co., St. Louis, Mo.), pH 7.5 and stored at 4° C. until use.

Alternatively, a soluble, truncated derivative of furin lacking the carboxyl-terminal 81 amino acids was used (see Molloy et al., ibid., incorporated by reference, for a more detailed description of this molecule). Briefly, BSC-40 cells were infected with a vaccinia virus vector containing the truncated furin cDNA, grown for 16–18 h in serum-free defined media and then harvested. The cells were disrupted and subjected sequentially to centrifugation at 1000 g and 10,000 g at 4° C. The supernatant was passed through a 0.2 $\mu$m filter and then diluted approximately 1:1 with a buffer consisting of 20 mM BisTris (pH 7.0) and 1 mM 2-mercaptoethanol. This mixture was then applied to a Mono Q HR 5/5 fast protein liquid chromatography anion exchange column (Pharmacia LKB Biotechnology Inc.) and the truncated furin derivative eluted with a gradient of 0–750 mM sodium chloride and stored at 4° C. until use.

EXAMPLE 2

In Vitro Mutagenesis and Production of Native and Variant Species of $\alpha_1$-Antitrypsin A novel $\alpha_1$-antitrypsin variant, termed $\alpha_1$-antitrypsin Portland (SEQ ID NO.: 9), was produced by in vitro mutagenesis of a cloned cDNA encoding the naturally-occurring variant $\alpha_1$-antitrypsin Pittsburgh (SEQ ID NO.: 12–13) (Lewis et al., 1978, Blood 51: 129–137; Owen et al., 1983, N. Engl. J. Med. 309: 694–698). A full length cDNA encoding $\alpha_1$-antitrypsin Pittsburgh (which is identical to the sequence disclosed in Long et al., supra, except for a $Met_{358}\rightarrow Arg_{358}$ mutation) was subcloned into M13mp19 phage using standard techniques (see Sambrook et al., ibid., Chapter 15). The following mutagenesis primer was then annealed to the sequence of single-stranded phage DNA corresponding to codons 352–358 of the $\alpha_1$-antitrypsin Pittsburgh sequence:

5'-TTTTTAGAGCGCATACCCAG-3' (SEQ ID NO.: 14)

The underlined sequence encodes the mutagenized codon. After annealing, the mutagenesis primer was extended using the Klenow fragment of *E. coli* DNA polymerase in the presence of the four deoxynucleotide triphosphates. Clones having the mutagenized sequence were then grown and selected in *E. coli,* and DNA sequencing of the appropriate portion of the sequence of selected mutagenized clones was performed to confirm successful mutagenesis. The mutagenized $\alpha_1$-antitrypsin cDNA sequences were then subcloned into the vaccinia virus recombination vector pZVneo and used to produce vaccinia virus recombinants as described in Example 1 (and described in more detail in Hayflick et al., 1992, J. Neurosci. 12: 705–717, hereby incorporated by reference).

As a result of mutagenesis, the sequence of $\alpha_1$-antitrypsin Pittsburgh ($Ala_{355}$-Ile-Pro-$Arg_{358}$) (SEQ ID NO.: 15) was changed to the novel sequence of $\alpha_1$-antitrypsin Portland ($Arg_{355}$-Ile-Pro-$Arg_{358}$) (SEQ ID NO.: 10). Vaccinia virus constructs containing native $\alpha_1$-antitrypsin (SEQ ID NOS.: 16 & 17) (VV:$\alpha_1$-NAT; $Ala_{335}$-Ile-Pro-$Met_{358}$) (SEQ ID NO.: 7), $\alpha_1$-antitrypsin Pittsburgh (SEQ ID NOS.: 12 & 13), (VV:$\alpha_1$-PIT) and $\alpha_1$-antitrypsin Portland (SEQ ID NOS.: 18 & 19) (VV:$\alpha_1$-PDX) were each used to infect BSC-40 cells. Such infected cells secrete each of the $\alpha_1$-antitrypsins into the culture media, and native $\alpha_1$-antitrypsin and variants were isolated from culture media from appropriately-infected BSC-40 cells by passage of such media over a Mono Q HR 5/5 high pressure liquid chromatography anion exchange column (Pharmacia LKB Biotechnology Ltd., Stockholm, Sweden) and eluted using a linear gradient (0.05→0.5M) of sodium chloride in 50 mM Tris-HCl (pH 8.0), as described further in Molloy et al. Production of native $\alpha_1$-antitrypsin (Lane 1) and variants Pittsburgh (Lane 2) and Portland (Lane 3) was confirmed by Western blot hybridization (see Sambrook et al., ibid., Chapter 18 ) as shown in FIG. 1.

EXAMPLE 3

In Vitro Characterization of Furin Endoprotease Inhibition by $\alpha_1$-Antitrypsin Portland $\alpha_1$-antitrypsin and variants Pittsburgh and Portland were assayed for the ability to inhibit furin endoprotease in vitro essentially as described in Molloy et al. (ibid.). Briefly, 25 $\mu$L of the resuspended furin preparation described in Example 1 was incubated with each of the $\alpha_1$-antitrypsins (at a final concentration of 10 $\mu$g/mL) for 20 min at 37° C. in a buffer comprising 100 mM HEPES (pH 7.5), 1 mM $CaCl_2$, 1 mM 2-mercaptoethanol and 0.5% Triton-X 100. Substrate ((N-butoxycarbonyl)-Arg-Val-Arg-(4-methylcoumaryl-7-amide); Peninsula Laboratories, Belmont, Calif.) was then added to a final concentration of 50 $\mu$M and incubated for 30 min at 37° C. The amount of liberated aminomethylcoumarin was then determined by fluorimetry (excitation wavelength=380 nm; emission wavelength=460 nm) using a spectrofluorimeter (Perkin Elmer, Waterbury, Conn. Model LS3). The results of this experiment are shown in FIG. 2. For comparison, each of the $\alpha_1$-antitrypsins were also incubated with thrombin and assayed for thrombin peptidase activity colorometrically using benzoyl-Phe-Val-Arg-(para-nitroanilide) as substrate. These results are also shown in FIG. 2. Native $\alpha_1$-antitrypsin was unable to inhibit either furin or thrombin endoprotease activity (striped bars). $\alpha_1$-antitrypsin Pittsburgh specifically inhibited thrombin but not furin (dotted bars). The novel variant $\alpha_1$-antitrypsin Portland (stipled bars) had no effect on thrombin endoprotease activity, but specifically and essentially quantitatively inhibited furin endoprotease activity. Table I provides the results of a comparison between the levels of inhibition of elastase (assayed colorometrically with

TABLE I

| Enzyme | Conc.[a] | $\alpha_1$-NAT[b] | $\alpha_1$-PIT[b] | $\alpha_1$-PDX[b] |
|---|---|---|---|---|
| Elastase | 100 | 13 | 98 | 101 |
| Thrombin | 100 | 94 | 8 | 95 |
| Furin | 100 | 101 | 97 | 0.04 |

[a] = relative concentration of each serpin inhibitor
[b] = percent endoprotease activity in presence of each serpin (N-butoxycarbonyl)-Ala-Ala-Pro-Ala-(para-nitroanilide) as substrate). Elastase activity was specifically inhibited by native $\alpha_1$-antitrypsin ($\alpha_1$-NAT), thrombin was specifically inhibited by $\alpha_1$-antitrypsin Pittsburgh ($\alpha_1$-PIT), and furin was specifically inhibited by $\alpha_1$-antitrypsin Portland ($\alpha_1$-PDX). $\alpha_1$-PDX was found to be greater than 300-fold more effective than $\alpha_1$-PIT in inhibiting furin, having a $K_{1/2}$ of 0.03 µg/mL, (equivalent to 0.4 nM). $\alpha_1$-PDX is also greatly attenuated in thrombin inhibitory activity (>300-fold) compared with $\alpha_1$-PIT. These results demonstrated that the novel $\alpha_1$-antitrypsin structural variant ($\alpha_1$-PDX) disclosed herein has novel functional properties that make it useful as a specific furin endoprotease inhibitor.

EXAMPLE 4

In Vivo Characterization of Furin Endoprotease Inhibition by $\alpha_1$-Antitrypsin Portland $\alpha_1$-antitrypsin Portland was assayed for the ability to inhibit furin endoprotease in vivo. BSC-40 cells were infected with a vaccinia virus vector encoding the $\alpha_1$-antitrypsin Portland as described in Example 2 and a vaccinia virus vector encoding pro-β-nerve growth factor (β-NGF), a neuropeptide growth factor known to be processed by furin at the consensus furin site -Arg-Ser-Lys-Arg↓- (SEQ ID NO.: 1) (Bresnahan et al., ibid.) and secreted into the cell growth media. Co-infected cells were incubated in the presence of ($^{35}$S)-methionine for 4 h after infection and the cell media harvested. Media samples were then immunoprecipitated with NGF-specific antibodies and assayed by sodium dodecyl sulfate/polyacrylamide gel electrophoresis (SDS-PAGE) and visualized by fluorography using standard techniques (as described in Sambrook et al., ibid.)

Figure 3:
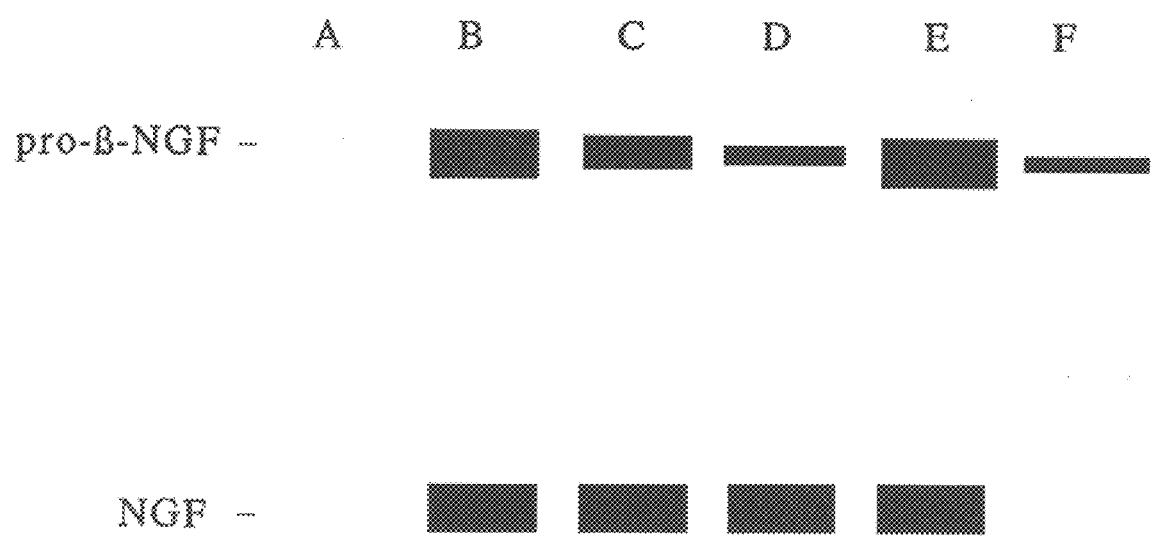
FIG. 3 is an SDS-PAGE analysis of inhibition showing proteolytic processing of pro-$\beta$-NGF by $\alpha_1$-antitrypsin and variants.

The results of these experiments are shown in FIG. 3. Cells infected with wild-type vaccinia virus secreted no detectable β-NGF into the culture media (Lane A), whereas cells infected with the vaccinia virus vector encoding β-NGF (Lane B) secreted both processed (13 kilodaltons, kD) and unprocessed (≈35 kD) forms of β-NGF; co-infection of such cells with wild-type vaccinia virus had no effect on this pattern of β-NGF production (Lane C). Similarly, BSC-40 cells co-infected with the β-NGF construct and with vaccinia virus constructs encoding native $\alpha_1$-antitrypsin (Lane D) and $\alpha_1$-antitrypsin Pittsburgh (Lane E) also produced both the processed and unprocessed forms of β-NGF. In contrast, cells co-infected with the β-NGF construct and with vaccinia virus constructs encoding $\alpha_1$-antitrypsin Portland (Lane F) produced only the unprocessed form of β-NGF, demonstrating that $\alpha_1$-antitrypsin Portland is capable of inhibiting furin-mediated endoprotease processing of bioactive pro-peptides in vivo.

EXAMPLE 5

Inhibition of Furin-Mediated Processing of Human Immunodeficiency Virus gp160 by $\alpha_1$-Antitrypsin Portland The experiments described in Example 4 were repeated using a vaccinia virus construct encoding the Human Immunodeficiency virus (HIV-1) glycoprotein gp160. This precursor protein is known to be proteolytically processed into two membrane-associated proteins: gp120 (which binds the HIV receptor CD4 on the cell surface of target host cells) and gp41 (which provides a fusogenic activity that mediates viral entry into the cell) in vivo. Proteolytic processing at the furin consensus site -Arg-Glu-Lys-Arg↓- (SEQ ID NO.: 3) is a necessary step in maturation and release of HIV viral particles. Cell membranes from cells infected with vaccinia virus constructs were isolated as described in Example 1. Proteins from such membrane preparations were resolved by SDS-PAGE and specifically identified by Western blot analysis (see Sambrook et al., ibid., Chapter 18) using antibodies against HIV proteins (see Anderson et al., supra).

Figure 4:
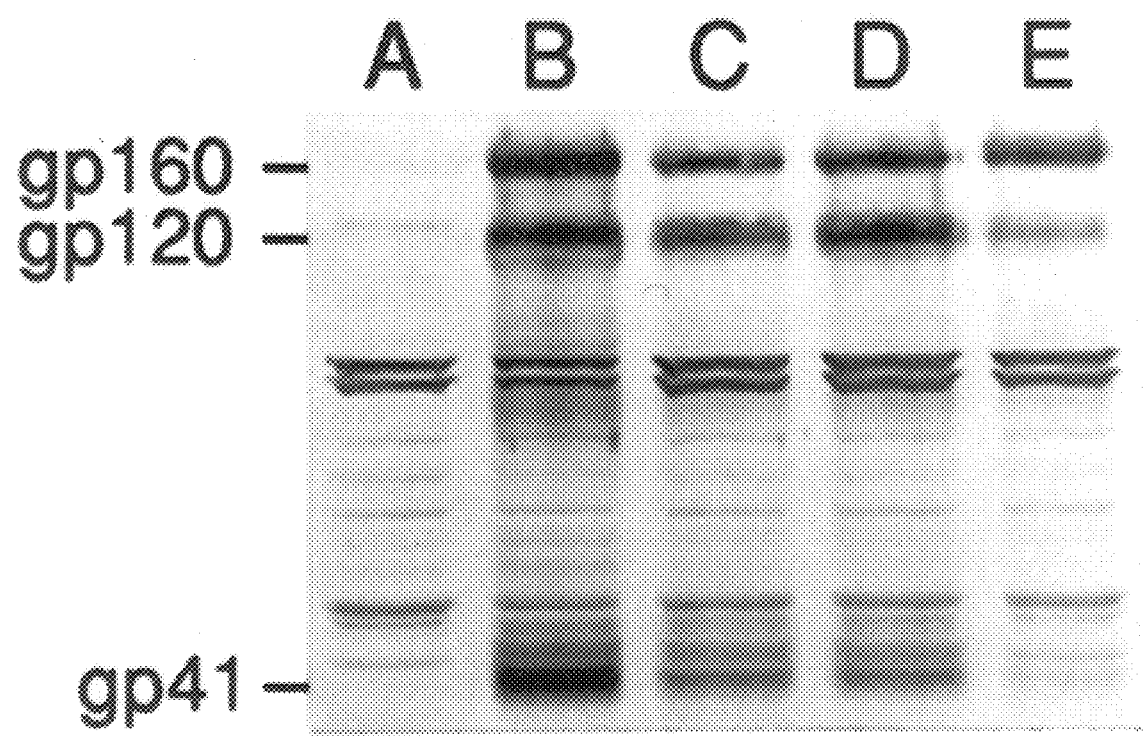
FIG. 4 depicts Western blot analysis showing inhibition of proteolytic processing of HIV gp160 by $\alpha_1$-antitrypsin and variants.

The results of this experiment are shown in FIG. 4. Cells infected with wild-type vaccinia virus produced no detectable HIV-related peptides (Lane A). In cells infected with the vaccinia virus vector encoding gp160, both the unprocessed protein and processing products, gp120 and gp41 were produced (Lane B). BSC-40 cells co-infected with the gp160 construct and with vaccinia virus constructs encoding native $\alpha_1$-antitrypsin (Lane C) and $\alpha_1$-antitrypsin Pittsburgh (Lane D) also produced both unprocessed gp160 and processed gp120 and gp41. Cells co-infected with the gp160 construct and with vaccinia virus constructs encoding $\alpha_1$-antitrypsin Portland (Lane E), on the other hand, produced only unprocessed gp160. These results demonstrated that $\alpha_1$-antitrypsin Portland is capable of inhibiting furin-mediated endoprotease processing of bioactive viral proteins in vivo, and immediately suggested a method for treating viral infection by inhibiting viral protein processing.

Figure 5:
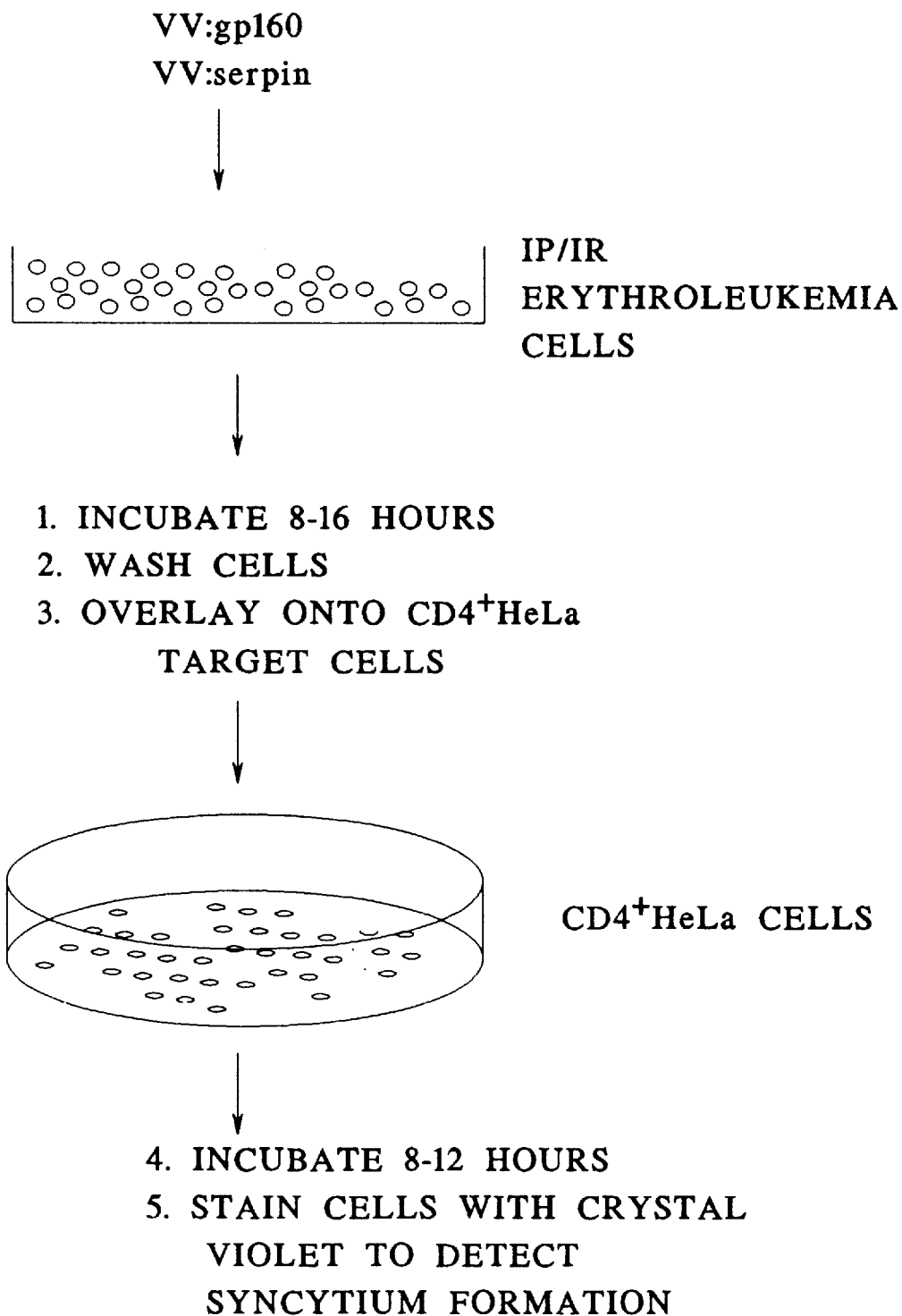
FIG. 5 illustrates the experimental protocol for assaying the gp41-mediated fusogenic capacity of gp160-producing IP/IR erythroleukemia cells to form syncytia with $CD4^+$ human HeLa cells in the presence and absence of co-expressed $\alpha_1$-antitrypsin and variants.

In another series of experiments, $\alpha_1$-antitrypsin Portland-mediated inhibition of proteolytic processing of gp160 was assayed to determine the functional consequences of such inhibition. As described above, processing of gp160 results in the production of gp41, a protein that provides a fusogenic activity important for viral entry into target cells. Expression of gp120 and gp41 on the surface of IP/IR erythroleukemia cells (see Spiro et al., 1988, J. Virol. 63: 4434–4437) promotes cell fusion and syncytium formation with cells expressing the gp120 target, CD4, at the cell surface. In these experiments, IP/IR cells were co-infected with vaccinia virus expression constructs encoding gp160 and each of the $\alpha_1$-antitrypsins to determine the effect of inhibition of gp160 processing on the fusogenic capacity of the cells. This experimental protocol is shown in FIG. 5. Briefly, IP/IR cells were co-infected with the vaccinia virus gp160 construct, either alone or co-infected with each of the $\alpha_1$-antitrypsin constructs described in Example 2. The cells were incubated for 8–16 hours, collected and then overlaid onto a monolayer of CD4$^+$ human HeLa cells a modification of parental HeLa cells (ATCC No. CCL 2) that express the CD4 cell surface protein, as described in Kabat et al., 1994, Virol. 202: 1058–1060. These cells were incubated for an additional 8–12 hours, and syncytium formation detected by staining with crystal violet and observed by phase-contrast microscopy.

The results of these experiments are shown in FIGS. 6A through 6F. FIG. 6A shows the results of HeLa/CD4$^+$ cell overlay with IP/IR cells infected with vaccinia virus recombinants encoding HIV gp160, and FIG. 6B shows results of HeLa/CD4$^+$ cell overlay experiments using IP/IR cells infected with HIV gp160 vaccinia recombinants co-infected with wild type vaccinia virus. Syncytia formation (and hence proper proteolytic processing of gp160 to gp120 and gp41) in the cells of each of these infected co-cultures was evidenced by the large number of multinucleated cells in each of the cultures. FIG. 6C shows the results of HeLa/CD4$^+$ cell overlay experiments using IP/IR cells infected with wild-type vaccinia virus; essentially no multinucleated cells were seen in such cultures. FIGS. 6D and 6E show the results of HeLa CD4$^+$ cell overlay experiments using IP/IR cells co-infected with vaccinia virus recombinants encoding gp160 and native (FIG. 6C) and the Pittsburgh variant (FIG. 6D) of $\alpha_1$-antitrypsin. Co-expression of native or variant Pittsburgh $\alpha_1$-antitrypsin had no effect on syncytia formation caused by gp41. FIG. 6F shows the effect on HIV gp41-mediated syncytia formation of HeLa CD4$^+$ cell overlay experiments using IP/IR cells co-infected with vaccinia virus recombinants encoding gp160 and $\alpha_1$-antitrypsin Portland in HeLa/CD4$^+$ cells. Syncytia formation is completely abolished in these cultures, and the cells of such cultures looked identical to cells in overlay experiments using IP/IR cells infected with wild-type vaccinia virus as seen in FIG. 6C. These results demonstrate that inhibition of gp160 processing by $\alpha_1$-antitrypsin Portland eliminates the fusogenic activity of viral gp41 and suggests that such inhibition may provide a method for treating HIV infection in vivo and in vitro.

EXAMPLE 6

Inhibition of Furin-Mediated Processing of β-Nerve Growth Factor by Direct Application of $\alpha_1$-Antitrypsin Portland The ability of $\alpha_1$-antitrypsin Portland to inhibit proteolytic processing by addition of the inhibitor to the cellular growth media was demonstrated in the following assay. BSC-40 cells were grown to confluence in 35 mm tissue culture plates (Falcon Microbiological Supply Co., Lincoln Park, N.J.) and then infected with recombinant vaccinia virus encoding a functional pro-β-NGF protein (VV:mNGF) as described in Example 4. Four hours prior to infection, the cellular growth media was removed and replaced with serum-free defined media (MCDB 202 media, made as described in McKeeton et al., 1977, Dev. Biol. Std. 37: 97–108) supplemented with either 0, 0.5 or 50 µg/mL $\alpha_1$-antitrypsin Portland ($\alpha_1$-PDX), prepared as described in Example 2. After this 4 h incubation, the cells were infected with VV:mNGF at a multiplicity of infection (m.o.i.) of 5 pfu/cell. In one culture, the pre-incubated cells were transfected with VV:mNGF at a m.o.i. of 2 and co-infected with VV:$\alpha_1$-PDX (see Example 2) at a m.o.i. of 5. After virus inoculation, $\alpha_1$-PDX was added to the culture media of each infected plate at the same concentration as in the pre-incubation period.

Eighteen hours post-infection the media was removed from each plate and the cells metabolically labeled by incubation for 5 h in media containing ($^{35}$S)-methionine and ($^{35}$S)-cysteine (500 µCi) and $\alpha_1$-PDX at the appropriate concentration for each plate. After labeling, the culture media from each plate was harvested and NGF peptides immunoprecipitated, resolved by SDS-PAGE and visualized by fluorography as described in Example 4.

Figure 7A:
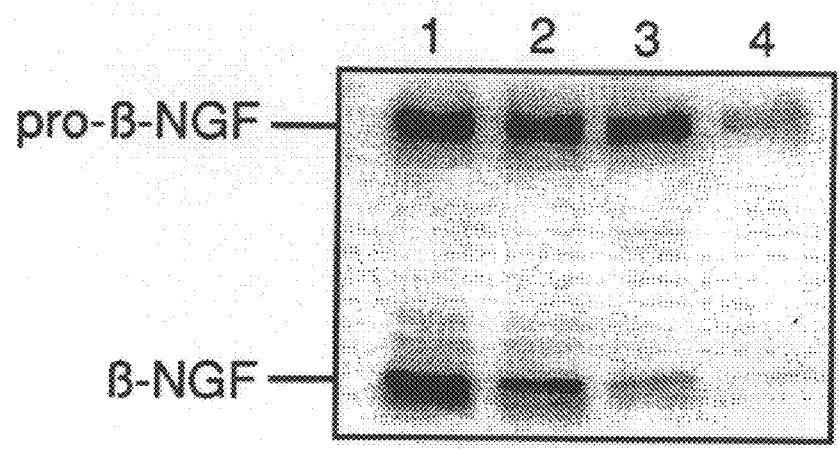
FIGS. 7A and 7B show an autoradiograph of $\alpha_1$-antitrypsin Portland-mediated inhibition of pro-$\beta$-NGF proteolytic processing in VV:mNGF-infected BSC-40 cells (FIG. 7A) and quantitation of these results as a percentage of the autoradiographic density of the processed band ($\beta$-NGF) relative to the total autoradiographic density (the sum of the $\beta$-NGF band plus the pro-$\beta$-NGF band).
Figure 7B:
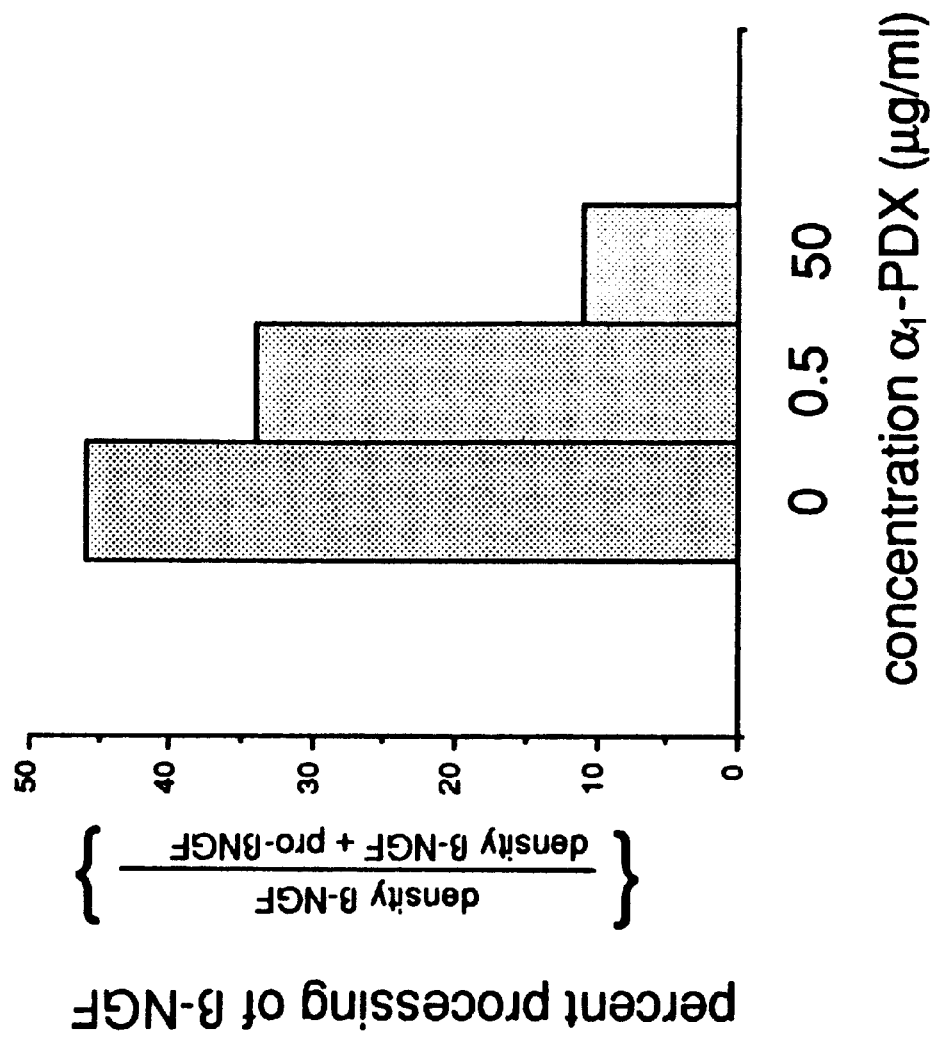

The results of this experiment are shown in FIGS 6A and 7B. FIG. 7A is an autoradiograph of SDS-PAGE analysis of immunoprecipitated NGF peptides from each of the infected cultures, in which lane 1 contains the results from the culture incubated with $\alpha_1$-PDX at 0 µg/mL; lane 2 contains the results from the culture incubated with $\alpha_1$-PDX at 0.5 µg/mL; lane 3 contains the results from the culture incubated with $\alpha_1$-PDX at 50 µg/mL; and lane 4 contains the results from the culture co-infected with VV:$\alpha_1$-PDX. As this autoradiographic evidence shows, incubation of cell cultures with $\alpha_1$-PDX protein resulted in marked attenuation of furin-directed proteolytic processing of pro-β-NGF in a dose-dependent manner. The autoradiographic data was quantitated by densitometry as shown in FIG. 7B; the percent relative amount of inhibition of proteolytic processing is represented as a percentage of the density of the processed (β-NGF) band relative to the density of the sum of the processed plus the unprocessed (pro-β-NGF) band. FIGS. 6A and 7B shows that $\alpha_1$-PDX at 50 µg/mL reduces the amount of proteolytic processing about five-fold (47% (0 µg/mL) versus 10% (50 µg/mL)). Essentially no processing is seen in the co-infected cell line, consistent with the results described in Example 4 above.

This dose-dependent attenuation of furin-directed proteolytic processing following administration of $\alpha_1$-PDX protein directly to cells in culture demonstrates the feasibility of a protein-based therapeutic approach directed at inhibiting furin-directed proteolytic maturation of a variety of biologically-important protein molecules, which is additionally advantageous due to the lack of thrombin inhibition exhibited by $\alpha_1$-PDX protein as disclosed herein.

EXAMPLE 7

Figure 8:
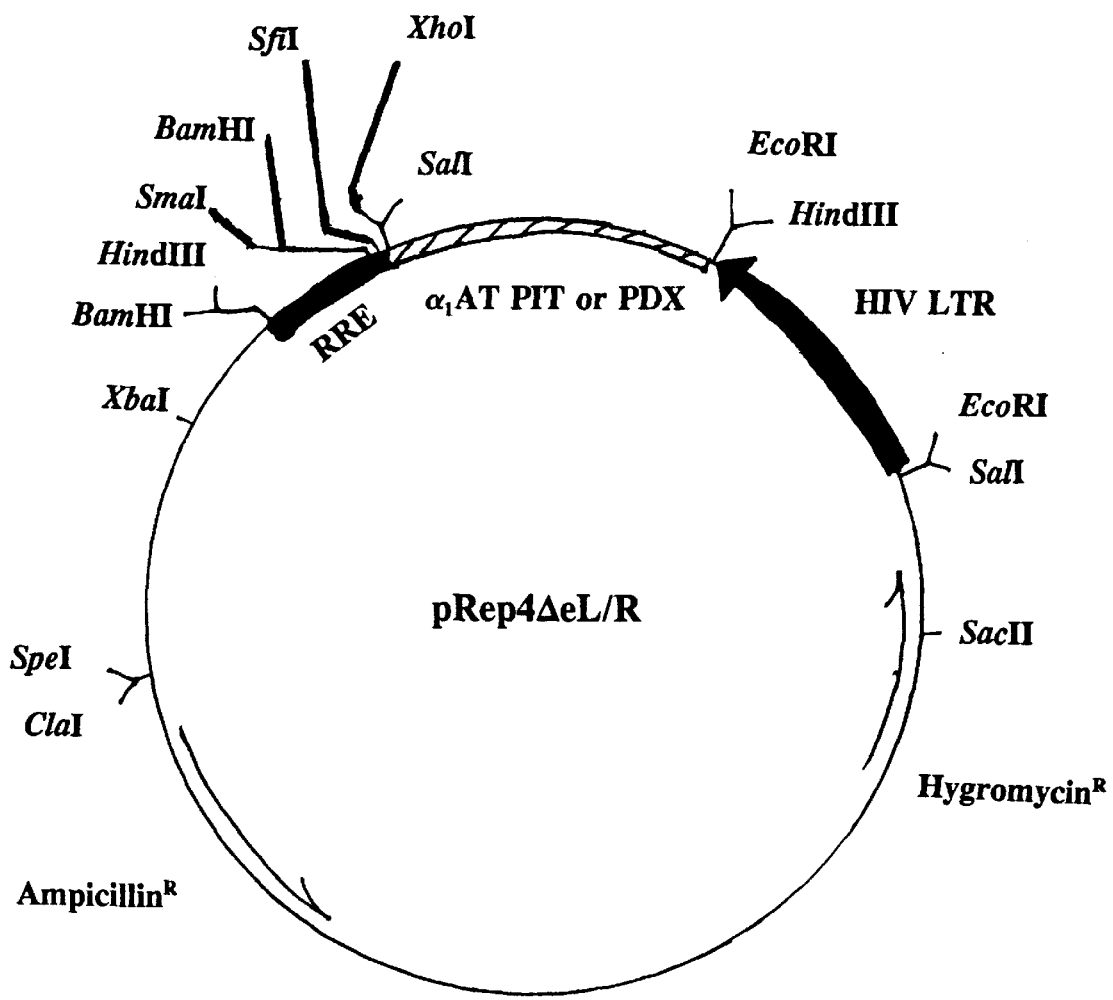
FIG. 8 depicts the structure of recombinant expression constructs pRep4$\Delta$L/Rp$\alpha_1$-PIT and pRep4$\Delta$L/Rp$\alpha_1$-PDX.

Construction of an HIV-LTR-based Recombinant Expression Vector Encoding $\alpha_1$-Antitrypsin Portland In order to stably transfect cells with a recombinant expression construct capable of expressing $\alpha_1$-PDX protein in vivo, the following expression vector was made, wherein expression of $\alpha_1$-PDX was mediated by the long terminal repeat (LTR) sequences of HIV-2. The completed plasmid is shown in FIG. 8.

A 470 bp fragment was excised from the recombinant plasmid pGEM/RRE by SmaI/HindIII digestion and then blunt-end cloned into the BamHI site of the plasmid pRep4 (Invitrogen, San Diego, Calif.). Restriction enzyme-generated overhangs were blunt-ended using Klenow polymerase (Pharmacia, Upsala, Sweden) using conventional techniques (see Sambrook et al.). The 470 bp fragment contains the rev responsive element of HIV-HXB2, comprising nucleotides 7621–8140 (Malim et al., 1989, Nature 338: 254–257). The Rous Sarcoma Virus 3' LTR was excised from the resulting plasmid by a SalI (partial blunt)/HindIII digest, and replaced by ligation with an EcoRI(blunt)/ HindIII digestion fragment from pBennCAT (NIH AIDS Research Program, Bethesda, Md.) containing the HIV LTR (nucleotides −450 to +80). The resulting expression plasmid was termed pRep4/RRE.

Plasmids capable of expressing $\alpha_1$-PIT or $\alpha_1$-PDX cDNAs were constructed by inserting each of the cDNA molecules into pRep4/RRE between the HIV LTR and the RRE sequence in the proper orientation. This was done by excising $\alpha_1$-PIT cDNA sequences from pA1AT PIT (Long et al., supra) using EcoRI (blunt) and XhoI digestion, or by excising $\alpha_1$-PDX cDNA sequences from pAIAT PDX using SmaI and XhoI digestion, and cloning each cDNA into HindIII (blunt)/XhaI-digested pRep4/RRE. In a final step, the Epstein Barr virus origin of replication (ORIP) and nuclear antigen (EBNA-1) sequences were excised from the final versions of each of the $\alpha_1$-antitrypsin variant expression constructs as follows. pRep4/RRE was digested with SpeI and ClaI, blunt-ended as described above, and religated to itself (see FIG. 8). A XbaI/SacII fragment from the pRep4/RRE plasmid so modified was then swapped for the corresponding fragment in each of the $\alpha_1$-antitrypsin variant plasmids described above, This resulted in plasmids having the structure illustrated in FIG. 8 and encoding each of the $\alpha_1$-antitrypsin variants $\alpha_1$-PIT (plasmid pRep4ΔL/Rp$\alpha_1$-PIT) and $\alpha_1$-PDX (plasmid pRep4ΔL/Rp$\alpha_1$-PDX).

EXAMPLE 8

Establishment of Human CD4$^+$ Cell Lines Expressing $\alpha_1$-Antitrypsin Portland The pRep4ΔL/Rp$\alpha_1$-PDX plasmid contains a functional hygromycin resistance gene (see FIG. 8) capable of conferring hygromycin resistance to eukaryotic cells (see Product Catalog, Invitrogen). Ten micrograms of this plasmid DNA were introduced into HeLa/CD4$^+$ clone 1022 cells (described in Example 5 above) using a modified calcium phosphate precipitation technique (Chen & Okayama, 1988, Molec. Cell. Biol. 8: 123–130, as further described in Sambrook et al., ibid.). Two days after transfection the cells were placed on selective media RPMI60/10% fetal calf serum supplemented with 100 μg/mL hygromycin (Sigma Chemical Co.) and maintained in this media throughout the experiment. Cell clones resistant to the drug appeared after about two weeks in selective media, and individual clones were isolated and expanded for subsequent experiments using conventional techniques (see *Tissue Culture,* Academic Press, Kruse & Patterson, editors (1973)). Two such clones (termed PDX-4 and PDX-6) were used in the following experiments.

Figure 9A:
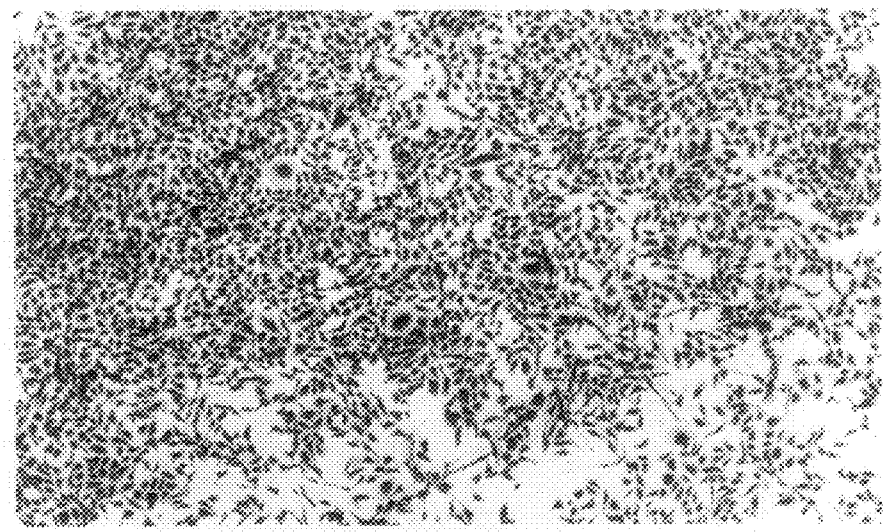
FIGS. 9A through 9C illustrates HIV-infected cultures of HeLa $CD4^+$ clone 1022 cells (FIG. 9B) and two independent transfectants, PDX-4 (FIG. 9C) and PDX-6 (FIG. 9A) four days post-infection.
Figure 9B:
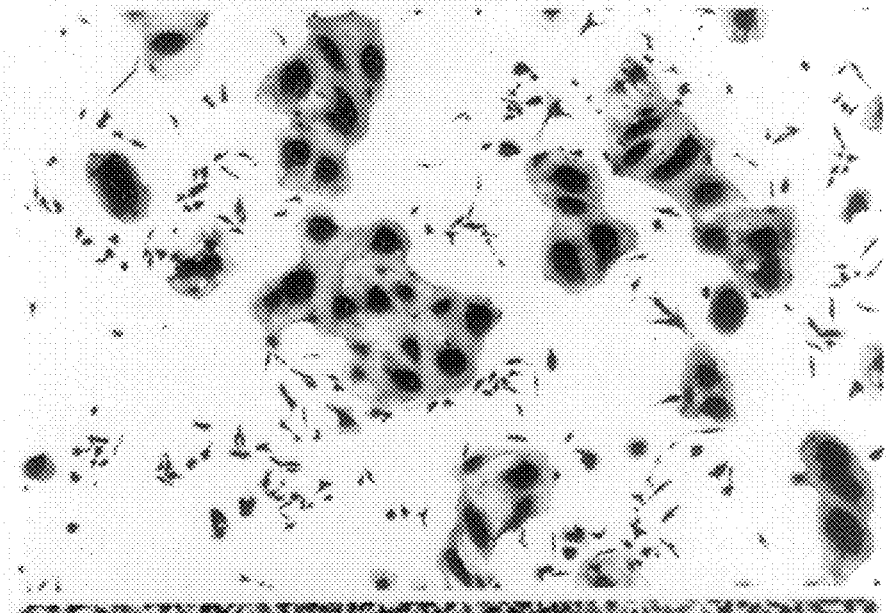
Figure 9C:
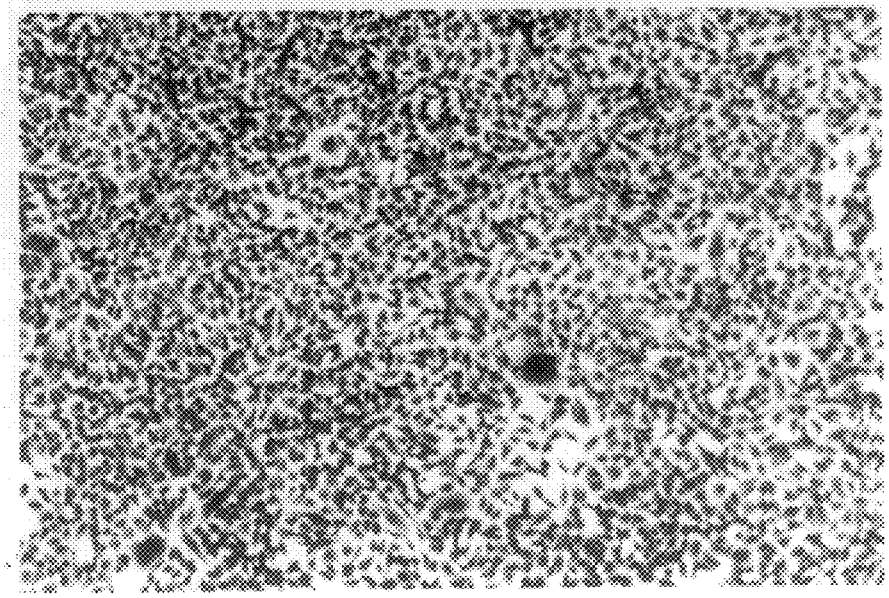

Cell lines PDX-4, PDX-6 and parental HeLa CD4$^+$ clone 1022 were seeded in 6-well plates (Falcon) at a density of 2×10$^5$ cells/plate. Cells cultures were then infected in duplicate with 2 mL of media containing HIV strain LAV (NIH AIDS Research Program) having a reverse transcriptase activity of about 70,000 cpm/mL. Cell cultures were examined four days post-infection for cytopathic effects and syncytia formation. Such cultures are shown in FIGS. 9A through 9C. The parental HeLa clone 1022 cells (FIG. 9B) exhibited numerous syncytia and cytopathic loss of the cell monolayer. Both PDX-4 (FIG. 9C) and PDX-6 (FIG. 9A) cell cultures, on the other hand, showed few syncytia. Productive infection was verified by the detection of more than 250 pg/mL of the HIV core antigen, p24, in supernatants from each of the infected cultures. The levels of infectious virus, in contrast, were much lower in the pDX-4 and PDX-6 cultures than in the parental HeLa clone 1022 culture. Cell lysates were prepared from each of the cell cultures on the fourth day post-infection and examined for the presence of gp160/gp120 Western blot analysis as described in Example 5. Both gp160 and bp120 were detected in HIV-infected HeLa clone 1022 cultures, while no gp120 and only a faint band corresponding to gp160 was found in HIV-infected PDX-4 and PDX-6 cultures.

These results demonstrated that expression of $\alpha_1$-PDX in HeLa clone 1022 cells conferred resistance in these cells to HIV infection. Moreover, the presence of p24 antigen in the cell supernatants of such cultures in the absence of large amounts of infectious virus indicates that expression of $\alpha_1$-antitrypsin Portland in these cells inhibits the formation of infectious enveloped virus particles. These results have important implications for preventing HIV infection of vulnerable cells both in vivo and in vitro.

It should be understood that the foregoing disclosure emphasizes certain specific embodiments of the invention and that all modifications or alternatives equivalent thereto are within the spirit and scope of the invention as set forth in the appended claims.

What we claim is:

1. A furin endoprotease inhibitor comprising a fragment of an $\alpha_1$-antitrypsin variant having an amino acid sequence comprising the amino acids -Arg-Xaa-Xaa-Arg-, wherein Xaa is any amino acid, at positions 355–358 of the native $\alpha_1$-antitrypsin amino acid sequence (SEQ ID No.: 6).

2. The furin endoprotease inhibitor of claim 1 comprising the amino acid sequence -Arg-Ile-Pro-Arg- (SEQ ID No.: 10).

3. A pharmaceutical composition comprising a therapeutically effective amount of a furin endoprotease inhibitor of claim 1 and a pharmaceutically acceptable carrier or diluent.

4. A homogenous composition of matter comprising a peptide fragment of $\alpha_1$-antitrypsin Portland (SEQ ID No.: 9) having an amino acid sequence comprising the amino acids -Arg-Xaa-Xaa-Arg-, wherein Xaa is any amino acid, at positions 355–358 of the native $\alpha_1$-antitrypsin amino acid sequence (SEQ ID No.: 6) and produced by a cell culture transformed with the recombinant expression construct comprising a nucleic acid encoding the fragment of $\alpha_1$-antitrypsin Portland that expresses the fragment of $\alpha_1$-antitrypsin Portland thereby.

5. A peptide having an amino acid sequence of 4 to 20 amino acids comprising the amino acid sequence -Arg-Xaa-Xaa-Arg-, wherein each Xaa is any amino acid.

6. A method of inhibiting viral infection of cells comprising contacting the cells with a peptide according to claim 5.

7. The method of claim 6 wherein the virus is cytomegalovirus.

8. A method of inhibiting bacterial infection of cells comprising contacting the cells with a peptide according to claim 5.

9. The method of claim 8 wherein the bacterial toxin is diphtheria toxin of *Corynebacterium diptheriae.*

10. The method of claim 8 wherein the bacterial toxin is anthrax toxin of *Bacillus anthracis.*

11. The method of claim 8 wherein the bacterial toxin is *Pseudomonas aerugenosa* exotoxin.

12. A method of blocking endoproteolytic activation of a bacterial toxin comprising the step of contacting a cell in the presence of the toxin with a furin endoprotease inhibitor comprising an $\alpha_1$-antitrypsin variant or peptide fragment thereof having an amino acid sequence comprising the amino acids -Arg-Xaa-Xaa-Arg-, wherein Xaa is any amino acid, at positions 355–358 of the native $\alpha_1$-antitrypsin amino acid sequence (SEQ ID No.: 6).

13. The method of claim 12 wherein the bacterial toxin is diphtheria toxin of *Cornyebacterium diptheriae.*

14. The method of claim 12 wherein the bacterial toxin is anthrax toxin of *Bacillus anthracis.*

15. The method of claim 12 wherein the bacterial toxin is *Pseudomonas aerugenosa* exotoxin.

16. A method of inhibiting bacterial infection of cells comprising contacting the cells with a furin endoprotease inhibitor comprising an $\alpha_1$-antitrypsin variant or peptide fragment thereof having an amino acid sequence comprising the amino acids -Arg-Xaa-Xaa-Arg-, wherein Xaa is any amino acid, at positions 355–358 of the native $\alpha_1$-antitrypsin amino acid sequence (SEQ ID NO.: 6).

17. A method of inhibiting viral infection of cells comprising contacting the cells with a furin endoprotease inhibitor comprising an $\alpha_1$-antitrypsin variant or peptide fragment thereof having an amino acid sequence comprising the amino acids -Arg-Xaa-Xaa-Arg-, wherein Xaa is any amino acid, at positions 355–358 of the native $\alpha_1$-antitrypsin amino acid sequence (SEQ ID No.: 6).

18. The method of claim 17 wherein the virus is cytomegalovirus.

* * * * *

```
                         SEQUENCE LISTING (1) GENERAL INFORMATION:

(iii) NUMBER OF SEQUENCES: 21

(2) INFORMATION FOR SEQ ID NO:1:

(i) SEQUENCE CHARACTERISTICS:
          (A) LENGTH: 4 amino acids
          (B) TYPE: amino acid
          (D) TOPOLOGY: linear (ii) MOLECULE TYPE: peptide (xi) SEQUENCE DESCRIPTION: SEQ ID NO:1:

Arg Ser Lys Arg
1

(2) INFORMATION FOR SEQ ID NO:2:

(i) SEQUENCE CHARACTERISTICS:
          (A) LENGTH: 4 amino acids
          (B) TYPE: amino acid
          (D) TOPOLOGY: linear (ii) MOLECULE TYPE: peptide (xi) SEQUENCE DESCRIPTION: SEQ ID NO:2:

Arg Pro Lys Arg
1

(2) INFORMATION FOR SEQ ID NO:3:

(i) SEQUENCE CHARACTERISTICS:
          (A) LENGTH: 4 amino acids
          (B) TYPE: amino acid
```

```
            (D) TOPOLOGY: linear (ii) MOLECULE TYPE: peptide (xi) SEQUENCE DESCRIPTION: SEQ ID NO:3:

Arg Glu Lys Arg
 1

(2) INFORMATION FOR SEQ ID NO:4:

(i) SEQUENCE CHARACTERISTICS:
            (A) LENGTH: 4 amino acids
            (B) TYPE: amino acid
            (D) TOPOLOGY: linear (ii) MOLECULE TYPE: peptide (xi) SEQUENCE DESCRIPTION: SEQ ID NO:4:

Arg Val Arg Arg
 1

(2) INFORMATION FOR SEQ ID NO:5:

(i) SEQUENCE CHARACTERISTICS:
            (A) LENGTH: 4 amino acids
            (B) TYPE: amino acid
            (D) TOPOLOGY: linear (ii) MOLECULE TYPE: peptide (ix) FEATURE:
            (A) NAME/KEY: Modified site
            (B) LOCATION: 2..3
            (C) OTHER INFORMATION: /label=Variable site
                 / note="The amino acid Xaa at position 2 can be
                 any amino acid; the amino acid Xaa at position 3
                 can be any amino acid."

(xi) SEQUENCE DESCRIPTION: SEQ ID NO:5:

Arg Xaa Xaa Arg
 1

(2) INFORMATION FOR SEQ ID NO:6:

(i) SEQUENCE CHARACTERISTICS:
            (A) LENGTH: 394 amino acids
            (B) TYPE: amino acid
            (D) TOPOLOGY: linear (ii) MOLECULE TYPE: protein (xi) SEQUENCE DESCRIPTION: SEQ ID NO:6:

Glu Asp Pro Gln Gly Asp Ala Ala Gln Lys Thr Asp Thr Ser His His
 1               5                  10                  15

Asp Gln Asp His Pro Thr Phe Asn Lys Ile Thr Pro Asn Leu Ala Glu
                20                  25                  30

Phe Ala Phe Ser Leu Tyr Arg Gln Leu Ala His Gln Ser Asn Ser Thr
            35                  40                  45

Asn Ile Phe Phe Ser Pro Val Ser Ile Ala Thr Ala Phe Ala Met Leu
        50                  55                  60

Ser Leu Gly Thr Lys Ala Asp Thr His Asp Glu Ile Leu Glu Gly Leu
 65                 70                  75                  80

Asn Phe Asn Leu Thr Gln Ile Pro Glu Ala Gln Ile His Glu Gly Phe
                85                  90                  95

Gln Glu Leu Leu Arg Thr Leu Asn Gln Pro Asp Ser Gln Leu Gln Leu
                100                 105                 110
```

```
Thr Thr Gly Asn Gly Leu Phe Leu Ser Gln Gly Leu Lys Leu Val Asp
        115                 120                 125

Lys Phe Leu Glu Asp Val Lys Lys Leu Tyr His Ser Glu Ala Phe Thr
    130                 135                 140

Val Asn Phe Gly Asp Thr Glu Gln Ala Lys Lys Gln Ile Asn Asp Tyr
145                 150                 155                 160

Val Glu Lys Gly Thr Gln Gly Lys Ile Val Asp Leu Val Lys Glu Leu
                165                 170                 175

Asp Arg Asp Thr Val Phe Ala Leu Val Asn Tyr Ile Phe Phe Lys Gly
            180                 185                 190

Lys Trp Glu Arg Pro Phe Glu Val Lys Asp Thr Glu Glu Asp Phe
        195                 200                 205

His Val Asp Gln Val Thr Thr Val Lys Val Pro Met Met Lys Arg Leu
    210                 215                 220

Gly Met Phe Asn Ile Gln His Cys Lys Lys Leu Ser Ser Trp Val Leu
225                 230                 235                 240

Leu Met Lys Tyr Leu Gly Asn Ala Thr Ala Ile Phe Phe Leu Pro Asp
            245                 250                 255

Glu Gly Lys Leu Gln His Leu Glu Asn Glu Leu Thr His Asp Ile Ile
                260                 265                 270

Thr Lys Phe Leu Glu Asn Glu Asp Arg Arg Ser Ala Ser Leu His Leu
    275                 280                 285

Pro Lys Leu Ser Ile Thr Gly Thr Tyr Asp Leu Lys Ser Val Leu Gly
        290                 295                 300

Gln Leu Gly Ile Thr Lys Val Phe Ser Asn Gly Ala Asp Leu Ser Gly
305                 310                 315                 320

Val Thr Glu Glu Ala Pro Leu Lys Leu Ser Lys Ala Val His Lys Ala
                325                 330                 335

Val Leu Thr Ile Asp Glu Lys Gly Thr Glu Ala Ala Gly Ala Met Phe
            340                 345                 350

Leu Glu Ala Ile Pro Met Ser Ile Pro Pro Glu Val Lys Phe Asn Lys
        355                 360                 365

Pro Phe Val Phe Leu Met Ile Glu Gln Asn Thr Lys Ser Pro Leu Phe
    370                 375                 380

Met Gly Lys Val Val Asn Pro Thr Gly Lys
385                 390
```

(2) INFORMATION FOR SEQ ID NO:7:

(i) SEQUENCE CHARACTERISTICS:
        (A) LENGTH: 4 amino acids
        (B) TYPE: amino acid
        (D) TOPOLOGY: linear (ii) MOLECULE TYPE: peptide (xi) SEQUENCE DESCRIPTION: SEQ ID NO:7:

```
Ala Ile Pro Met
1
```

(2) INFORMATION FOR SEQ ID NO:8:

(i) SEQUENCE CHARACTERISTICS:
        (A) LENGTH: 4 amino acids
        (B) TYPE: amino acid
        (D) TOPOLOGY: linear (ii) MOLECULE TYPE: peptide (ix) FEATURE:
            (A) NAME/KEY: Modified site
            (B) LOCATION: 2..3
            (C) OTHER INFORMATION: /label=Variable site
                / note="The amino acid Xaa at position 2 can be
                any amino acid; the amino acid Xaa at position 3
                can be any amino acid."

(xi) SEQUENCE DESCRIPTION: SEQ ID NO:8:

Arg Xaa Xaa Arg
1

(2) INFORMATION FOR SEQ ID NO:9:

(i) SEQUENCE CHARACTERISTICS:
            (A) LENGTH: 394 amino acids
            (B) TYPE: amino acid
            (D) TOPOLOGY: linear (ii) MOLECULE TYPE: protein (ix) FEATURE:
            (A) NAME/KEY: Modified site
            (B) LOCATION: 355..358
            (C) OTHER INFORMATION: /label=Variant
                / note="The amino acid sequence is the amino acid
                sequence of the modified alpha-1-antitrypsin
                protein, alpha-1-antitrypsin Portland."

(xi) SEQUENCE DESCRIPTION: SEQ ID NO:9:

Glu Asp Pro Gln Gly Asp Ala Ala Gln Lys Thr Asp Thr Ser His His
1               5                  10                  15

Asp Gln Asp His Pro Thr Phe Asn Lys Ile Thr Pro Asn Leu Ala Glu
            20                  25                  30

Phe Ala Phe Ser Leu Tyr Arg Gln Leu Ala His Gln Ser Asn Ser Thr
        35                  40                  45

Asn Ile Phe Phe Ser Pro Val Ser Ile Ala Thr Ala Phe Ala Met Leu
    50                  55                  60

Ser Leu Gly Thr Lys Ala Asp Thr His Asp Glu Ile Leu Glu Gly Leu
65                  70                  75                  80

Asn Phe Asn Leu Thr Gln Ile Pro Glu Ala Gln Ile His Glu Gly Phe
                85                  90                  95

Gln Glu Leu Leu Arg Thr Leu Asn Gln Pro Asp Ser Gln Leu Gln Leu
            100                 105                 110

Thr Thr Gly Asn Gly Leu Phe Leu Ser Gln Gly Leu Lys Leu Val Asp
        115                 120                 125

Lys Phe Leu Glu Asp Val Lys Lys Leu Tyr His Ser Glu Ala Phe Thr
130                 135                 140

Val Asn Phe Gly Asp Thr Glu Gln Ala Lys Lys Gln Ile Asn Asp Tyr
145                 150                 155                 160

Val Glu Lys Gly Thr Gln Gly Lys Ile Val Asp Leu Val Lys Glu Leu
                165                 170                 175

Asp Arg Asp Thr Val Phe Ala Leu Val Asn Tyr Ile Phe Phe Lys Gly
            180                 185                 190

Lys Trp Glu Arg Pro Phe Glu Val Lys Asp Thr Glu Glu Glu Asp Phe
        195                 200                 205

His Val Asp Gln Val Thr Thr Val Lys Val Pro Met Met Lys Arg Leu
    210                 215                 220

Gly Met Phe Asn Ile Gln His Cys Lys Lys Leu Ser Ser Trp Val Leu
225                 230                 235                 240

-continued

```
Leu Met Lys Tyr Leu Gly Asn Ala Thr Ala Ile Phe Phe Leu Pro Asp
                245                 250                 255
Glu Gly Lys Leu Gln His Leu Glu Asn Glu Leu Thr His Asp Ile Ile
            260                 265                 270
Thr Lys Phe Leu Glu Asn Glu Asp Arg Arg Ser Ala Ser Leu His Leu
        275                 280                 285
Pro Lys Leu Ser Ile Thr Gly Thr Tyr Asp Leu Lys Ser Val Leu Gly
    290                 295                 300
Gln Leu Gly Ile Thr Lys Val Phe Ser Asn Gly Ala Asp Leu Ser Gly
305                 310                 315                 320
Val Thr Glu Glu Ala Pro Leu Lys Leu Ser Lys Ala Val His Lys Ala
                325                 330                 335
Val Leu Thr Ile Asp Glu Lys Gly Thr Glu Ala Ala Gly Ala Met Phe
            340                 345                 350
Leu Glu Arg Ile Pro Arg Ser Ile Pro Pro Glu Val Lys Phe Asn Lys
        355                 360                 365
Pro Phe Val Phe Leu Met Ile Glu Gln Asn Thr Lys Ser Pro Leu Phe
    370                 375                 380
Met Gly Lys Val Val Asn Pro Thr Gly Lys
385                 390
```

(2) INFORMATION FOR SEQ ID NO:10:

(i) SEQUENCE CHARACTERISTICS:
        (A) LENGTH: 4 amino acids
        (B) TYPE: amino acid
        (D) TOPOLOGY: linear (ii) MOLECULE TYPE: peptide (xi) SEQUENCE DESCRIPTION: SEQ ID NO:10:

```
Arg Ile Pro Arg
1
```

(2) INFORMATION FOR SEQ ID NO:11:

(i) SEQUENCE CHARACTERISTICS:
        (A) LENGTH: 394 amino acids
        (B) TYPE: amino acid
        (D) TOPOLOGY: linear (ii) MOLECULE TYPE: protein (ix) FEATURE:
        (A) NAME/KEY: Modified site
        (B) LOCATION: 355..358
        (C) OTHER INFORMATION: /label=Variant
            / note="The amino acid sequence is the amino acid
            sequence of the modified alpha-1-antitrypsin
            protein, alpha-1-antitrypsin Pittsburgh."

(xi) SEQUENCE DESCRIPTION: SEQ ID NO:11:

```
Glu Asp Pro Gln Gly Asp Ala Ala Gln Lys Thr Asp Thr Ser His His
1               5                  10                  15
Asp Gln Asp His Pro Thr Phe Asn Lys Ile Thr Pro Asn Leu Ala Glu
            20                  25                  30
Phe Ala Phe Ser Leu Tyr Arg Gln Leu Ala His Gln Ser Asn Ser Thr
        35                  40                  45
Asn Ile Phe Phe Ser Pro Val Ser Ile Ala Thr Ala Phe Ala Met Leu
    50                  55                  60
Ser Leu Gly Thr Lys Ala Asp Thr His Asp Glu Ile Leu Glu Gly Leu
65                  70                  75                  80
```

Asn Phe Asn Leu Thr Gln Ile Pro Glu Ala Gln Ile His Glu Gly Phe
            85                  90                  95

Gln Glu Leu Leu Arg Thr Leu Asn Gln Pro Asp Ser Gln Leu Gln Leu
            100                 105                 110

Thr Thr Gly Asn Gly Leu Phe Leu Ser Gln Gly Leu Lys Leu Val Asp
            115                 120                 125

Lys Phe Leu Glu Asp Val Lys Lys Leu Tyr His Ser Glu Ala Phe Thr
            130                 135                 140

Val Asn Phe Gly Asp Thr Glu Gln Ala Lys Lys Gln Ile Asn Asp Tyr
145                 150                 155                 160

Val Glu Lys Gly Thr Gln Gly Lys Ile Val Asp Leu Val Lys Glu Leu
            165                 170                 175

Asp Arg Asp Thr Val Phe Ala Leu Val Asn Tyr Ile Phe Phe Lys Gly
            180                 185                 190

Lys Trp Glu Arg Pro Phe Glu Val Lys Asp Thr Glu Glu Glu Asp Phe
            195                 200                 205

His Val Asp Gln Val Thr Thr Val Lys Val Pro Met Met Lys Arg Leu
            210                 215                 220

Gly Met Phe Asn Ile Gln His Cys Lys Lys Leu Ser Ser Trp Val Leu
225                 230                 235                 240

Leu Met Lys Tyr Leu Gly Asn Ala Thr Ala Ile Phe Phe Leu Pro Asp
            245                 250                 255

Glu Gly Lys Leu Gln His Leu Glu Asn Glu Leu Thr His Asp Ile Ile
            260                 265                 270

Thr Lys Phe Leu Glu Asn Glu Asp Arg Arg Ser Ala Ser Leu His Leu
            275                 280                 285

Pro Lys Leu Ser Ile Thr Gly Thr Tyr Asp Leu Lys Ser Val Leu Gly
            290                 295                 300

Gln Leu Gly Ile Thr Lys Val Phe Ser Asn Gly Ala Asp Leu Ser Gly
305                 310                 315                 320

Val Thr Glu Glu Ala Pro Leu Lys Leu Ser Lys Ala Val His Lys Ala
            325                 330                 335

Val Leu Thr Ile Asp Glu Lys Gly Thr Glu Ala Ala Gly Ala Met Phe
            340                 345                 350

Leu Glu Ala Ile Pro Arg Ser Ile Pro Pro Glu Val Lys Phe Asn Lys
            355                 360                 365

Pro Phe Val Phe Leu Met Ile Glu Gln Asn Thr Lys Ser Pro Leu Phe
            370                 375                 380

Met Gly Lys Val Val Asn Pro Thr Gly Lys
385                 390

(2) INFORMATION FOR SEQ ID NO:12:

(i) SEQUENCE CHARACTERISTICS:
        (A) LENGTH: 1356 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 34..1275
        (C) OTHER INFORMATION: /product= alpha-1-antitrypsin
            variant Pittsburgh"
            / standard_name= alpha-1-antitrypsin Pittsburgh (xi) SEQUENCE DESCRIPTION: SEQ ID NO:12:

```
GCACCACCAC TGACCTGGGA CAGTGAATCG ACA ATG CCG TCT TCT GTC TCG TGG        54
                                    Met Pro Ser Ser Val Ser Trp
                                    1               5

GGC ATC CTC CTG CTG GCA GGC CTG TGC TGC CTG GTC CCT GTC TCC CTG        102
Gly Ile Leu Leu Leu Ala Gly Leu Cys Cys Leu Val Pro Val Ser Leu
            10                  15                  20

GCT GAG GAT CCC CAG GGA GAT GCT GCC CAG AAG ACA GAT ACA TCC CAC        150
Ala Glu Asp Pro Gln Gly Asp Ala Ala Gln Lys Thr Asp Thr Ser His
    25                  30                  35

CAT GAT CAG GAT CAC CCA ACC TTC AAC AAG ATC ACC CCC AAC CTG GCT        198
His Asp Gln Asp His Pro Thr Phe Asn Lys Ile Thr Pro Asn Leu Ala
40                  45                  50                  55

GAG TTC GCC TTC AGC CTA TAC CGC CAG CTG GCA CAC CAG TCC AAC AGC        246
Glu Phe Ala Phe Ser Leu Tyr Arg Gln Leu Ala His Gln Ser Asn Ser
                60                  65                  70

ACC AAT ATC TTC TTC TCC CCA GTG AGC ATC GCT ACA GCC TTT GCA ATG        294
Thr Asn Ile Phe Phe Ser Pro Val Ser Ile Ala Thr Ala Phe Ala Met
            75                  80                  85

CTC TCC CTG GGG ACC AAG GCT GAC ACT CAC GAT GAA ATC CTG GAG GGC        342
Leu Ser Leu Gly Thr Lys Ala Asp Thr His Asp Glu Ile Leu Glu Gly
            90                  95                  100

CTG AAT TTC AAC CTC ACG GAG ATT CCG GAG CCT CAG ATC CAT GAA GGC        390
Leu Asn Phe Asn Leu Thr Glu Ile Pro Glu Pro Gln Ile His Glu Gly
    105                 110                 115

TTC CAG GAA CTC CTC CGT ACC CTC AAC CAG CTC CAG CTG ACC ACC GGC        438
Phe Gln Glu Leu Leu Arg Thr Leu Asn Gln Leu Gln Leu Thr Thr Gly
120                 125                 130                 135

AAT GGC CTG TTC CTC AGC GAG GGC CTG AAG CTA GTG GAT AAG TTT TTG        486
Asn Gly Leu Phe Leu Ser Glu Gly Leu Lys Leu Val Asp Lys Phe Leu
                140                 145                 150

GAG GAT GTT AAA AAG TTG TAC CAC TCA GAA GCC TTC ACT GTC AAC TTC        534
Glu Asp Val Lys Lys Leu Tyr His Ser Glu Ala Phe Thr Val Asn Phe
                155                 160                 165

GGG GAC ACC GAA GAG GCC AAG AAA CAG ATC AAC GAT TAC GTG GAG AAG        582
Gly Asp Thr Glu Glu Ala Lys Lys Gln Ile Asn Asp Tyr Val Glu Lys
            170                 175                 180

GGT ACT CAA GGG AAA ATT GTG GAT TTG GTC AAG GAG CTT GAC AGA GAC        630
Gly Thr Gln Gly Lys Ile Val Asp Leu Val Lys Glu Leu Asp Arg Asp
    185                 190                 195

ACA GTT TTT GCT CTG GTG AAT TAC ATC TTC TTT AAA GGC AAA TGG GAG        678
Thr Val Phe Ala Leu Val Asn Tyr Ile Phe Phe Lys Gly Lys Trp Glu
200                 205                 210                 215

AGA CCC TTT GAA GTC AAG GAC ACC GAG GAA GAG GAC TTC CAC GTG GAC        726
Arg Pro Phe Glu Val Lys Asp Thr Glu Glu Glu Asp Phe His Val Asp
                220                 225                 230

CAG GTG ACC ACC GTG AAG GTG CCT ATG ATG AAG CGT TTA GGC ATG TTT        774
Gln Val Thr Thr Val Lys Val Pro Met Met Lys Arg Leu Gly Met Phe
                235                 240                 245

AAC ATC CAG CAC TGT AAG AAG CTG TCC AGC TGG GTG CTG CTG ATG AAA        822
Asn Ile Gln His Cys Lys Lys Leu Ser Ser Trp Val Leu Leu Met Lys
            250                 255                 260

TAC CTG GGC AAT GCC ACC GCC ATG TTC TTC CTG CCT GAT GAG GGG AAA        870
Tyr Leu Gly Asn Ala Thr Ala Met Phe Phe Leu Pro Asp Glu Gly Lys
            265                 270                 275

CTA CAG CAC CTG GAA AAT GAA CTC ACC CAC GAT ATC ATC ACC AAG TTC        918
Leu Gln His Leu Glu Asn Glu Leu Thr His Asp Ile Ile Thr Lys Phe
280                 285                 290                 295

CTG GAA AAT GAA GAC AGA AGG TCT GCC AGC TTA CAT TTA CCC AAA CTG        966
```

```
Leu Glu Asn Glu Asp Arg Arg Ser Ala Ser Leu His Leu Pro Lys Leu
                300                 305                 310

TCC ATT ACT GGA ACC TAT GAT CTG AAG AGC GTC CTG GGT CAA CTG GGC        1014
Ser Ile Thr Gly Thr Tyr Asp Leu Lys Ser Val Leu Gly Gln Leu Gly
            315                 320                 325

ATC ACT AAG GTC TTC AGC AAT GGG GCT GAC CTC TCC GGG GTC ACA GAG        1062
Ile Thr Lys Val Phe Ser Asn Gly Ala Asp Leu Ser Gly Val Thr Glu
        330                 335                 340

GAG GCA CCC CTG AAG CTC TCC AAG GCC GTG CAT AAG GCT GTG CTG ACC        1110
Glu Ala Pro Leu Lys Leu Ser Lys Ala Val His Lys Ala Val Leu Thr
    345                 350                 355

ATC GAC GAG AAA GGG ACT GAA GCT GCT GGG GCC ATG TTT TTA GAG GCC        1158
Ile Asp Glu Lys Gly Thr Glu Ala Ala Gly Ala Met Phe Leu Glu Ala
360                 365                 370                 375

ATA CCC AGG TCT ATC CCC CCC GAG GTC AAG TTC AAC AAA CCC TTT GTC        1206
Ile Pro Arg Ser Ile Pro Pro Glu Val Lys Phe Asn Lys Pro Phe Val
                380                 385                 390

TTC TTA ATG ATT GAA CAA AAT ACC AAG TCT CCC CTC TTC ATG GGA AAA        1254
Phe Leu Met Ile Glu Gln Asn Thr Lys Ser Pro Leu Phe Met Gly Lys
            395                 400                 405

GTG GTG AAT CCC ACC CAA AAA TAACTGCTCG CTCCTCAACC CCTCCCCTCC           1305
Val Val Asn Pro Thr Gln Lys
        410

ATCCCTGGCC CCCTCCCTGG ATGACATTAA AGAAGGGTTG AGCTGGAAAA A               1356

(2) INFORMATION FOR SEQ ID NO:13:

(i) SEQUENCE CHARACTERISTICS:
        (A) LENGTH: 414 amino acids
        (B) TYPE: amino acid
        (D) TOPOLOGY: linear (ii) MOLECULE TYPE: protein (xi) SEQUENCE DESCRIPTION: SEQ ID NO:13:

Met Pro Ser Ser Val Ser Trp Gly Ile Leu Leu Leu Ala Gly Leu Cys
1               5                   10                  15

Cys Leu Val Pro Val Ser Leu Ala Glu Asp Pro Gln Gly Asp Ala Ala
                20                  25                  30

Gln Lys Thr Asp Thr Ser His His Asp Gln Asp His Pro Thr Phe Asn
            35                  40                  45

Lys Ile Thr Pro Asn Leu Ala Glu Phe Ala Phe Ser Leu Tyr Arg Gln
        50                  55                  60

Leu Ala His Gln Ser Asn Ser Thr Asn Ile Phe Phe Ser Pro Val Ser
65                  70                  75                  80

Ile Ala Thr Ala Phe Ala Met Leu Ser Leu Gly Thr Lys Ala Asp Thr
                85                  90                  95

His Asp Glu Ile Leu Glu Gly Leu Asn Phe Asn Leu Thr Glu Ile Pro
            100                 105                 110

Glu Pro Gln Ile His Glu Gly Phe Gln Glu Leu Leu Arg Thr Leu Asn
        115                 120                 125

Gln Leu Gln Leu Thr Thr Gly Asn Gly Leu Phe Leu Ser Glu Gly Leu
    130                 135                 140

Lys Leu Val Asp Lys Phe Leu Glu Asp Val Lys Lys Leu Tyr His Ser
145                 150                 155                 160

Glu Ala Phe Thr Val Asn Phe Gly Asp Thr Glu Glu Ala Lys Lys Gln
                165                 170                 175

Ile Asn Asp Tyr Val Glu Lys Gly Thr Gln Gly Lys Ile Val Asp Leu
```

```
                180             185             190
Val Lys Glu Leu Asp Arg Asp Thr Val Phe Ala Leu Val Asn Tyr Ile
            195             200             205
Phe Phe Lys Gly Lys Trp Glu Arg Pro Phe Glu Val Lys Asp Thr Glu
    210             215             220
Glu Glu Asp Phe His Val Asp Gln Val Thr Thr Val Lys Val Pro Met
225             230             235             240
Met Lys Arg Leu Gly Met Phe Asn Ile Gln His Cys Lys Lys Leu Ser
                245             250             255
Ser Trp Val Leu Leu Met Lys Tyr Leu Gly Asn Ala Thr Ala Met Phe
            260             265             270
Phe Leu Pro Asp Glu Gly Lys Leu Gln His Leu Glu Asn Glu Leu Thr
    275             280             285
His Asp Ile Ile Thr Lys Phe Leu Glu Asn Glu Asp Arg Arg Ser Ala
290             295             300
Ser Leu His Leu Pro Lys Leu Ser Ile Thr Gly Thr Tyr Asp Leu Lys
305             310             315             320
Ser Val Leu Gly Gln Leu Gly Ile Thr Lys Val Phe Ser Asn Gly Ala
                325             330             335
Asp Leu Ser Gly Val Thr Glu Glu Ala Pro Leu Lys Leu Ser Lys Ala
            340             345             350
Val His Lys Ala Val Leu Thr Ile Asp Glu Lys Gly Thr Glu Ala Ala
    355             360             365
Gly Ala Met Phe Leu Glu Ala Ile Pro Arg Ser Ile Pro Pro Glu Val
    370             375             380
Lys Phe Asn Lys Pro Phe Val Phe Leu Met Ile Glu Gln Asn Thr Lys
385             390             395             400
Ser Pro Leu Phe Met Gly Lys Val Val Asn Pro Thr Gln Lys
                405             410
```

(2) INFORMATION FOR SEQ ID NO:14:

(i) SEQUENCE CHARACTERISTICS:
        (A) LENGTH: 20 base pairs
        (B) TYPE: nucleic acid
        (C) STRANDEDNESS:single
        (D) TOPOLOGY: linear (ii) MOLECULE TYPE: cDNA (xi) SEQUENCE DESCRIPTION: SEQ ID NO:14:

TTTTTAGAGC GCATACCCAG                                   20

(2) INFORMATION FOR SEQ ID NO:15:

(i) SEQUENCE CHARACTERISTICS:
        (A) LENGTH: 4 amino acids
        (B) TYPE: amino acid
        (D) TOPOLOGY: linear (ii) MOLECULE TYPE: peptide (xi) SEQUENCE DESCRIPTION: SEQ ID NO:15:

Arg Ile Pro Arg
1

(2) INFORMATION FOR SEQ ID NO:16:

(i) SEQUENCE CHARACTERISTICS:
        (A) LENGTH: 1356 base pairs

-continued (B) TYPE: nucleic acid
(C) STRANDEDNESS: single
(D) TOPOLOGY: linear (ii) MOLECULE TYPE: cDNA (ix) FEATURE:
(A) NAME/KEY: CDS
(B) LOCATION: 34..1275
(C) OTHER INFORMATION: /product= alpha-1-antitrypsin wild-type sequence"
    / standard_name= alpha-1-antitrypsin (xi) SEQUENCE DESCRIPTION: SEQ ID NO:16:

```
CACCACCAC TGACCTGGGA CAGTGAATCG ACA ATG CCG TCT TCT GTC TCG TGG        54
                                    Met Pro Ser Ser Val Ser Trp
                                     1               5

GGC ATC CTC CTG CTG GCA GGC CTG TGC TGC CTG GTC CCT GTC TCC CTG       102
Gly Ile Leu Leu Leu Ala Gly Leu Cys Cys Leu Val Pro Val Ser Leu
         10                  15                  20

GCT GAG GAT CCC CAG GGA GAT GCT GCC CAG AAG ACA GAT ACA TCC CAC       150
Ala Glu Asp Pro Gln Gly Asp Ala Ala Gln Lys Thr Asp Thr Ser His
 25                  30                  35

CAT GAT CAG GAT CAC CCA ACC TTC AAC AAG ATC ACC CCC AAC CTG GCT       198
His Asp Gln Asp His Pro Thr Phe Asn Lys Ile Thr Pro Asn Leu Ala
 40                  45                  50                  55

GAG TTC GCC TTC AGC CTA TAC CGC CAG CTG GCA CAC CAG TCC AAC AGC       246
Glu Phe Ala Phe Ser Leu Tyr Arg Gln Leu Ala His Gln Ser Asn Ser
             60                  65                  70

ACC AAT ATC TTC TTC TCC CCA GTG AGC ATC GCT ACA GCC TTT GCA ATG       294
Thr Asn Ile Phe Phe Ser Pro Val Ser Ile Ala Thr Ala Phe Ala Met
                 75                  80                  85

CTC TCC CTG GGG ACC AAG GCT GAC ACT CAC GAT GAA ATC CTG GAG GGC       342
Leu Ser Leu Gly Thr Lys Ala Asp Thr His Asp Glu Ile Leu Glu Gly
         90                  95                 100

CTG AAT TTC AAC CTC ACG GAG ATT CCG GAG CCT CAG ATC CAT GAA GGC       390
Leu Asn Phe Asn Leu Thr Glu Ile Pro Glu Pro Gln Ile His Glu Gly
    105                 110                 115

TTC CAG GAA CTC CTC CGT ACC CTC AAC CAG CTC CAG CTG ACC ACC GGC       438
Phe Gln Glu Leu Leu Arg Thr Leu Asn Gln Leu Gln Leu Thr Thr Gly
120                 125                 130                 135

AAT GGC CTG TTC CTC AGC GAG GGC CTG AAG CTA GTG GAT AAG TTT TTG       486
Asn Gly Leu Phe Leu Ser Glu Gly Leu Lys Leu Val Asp Lys Phe Leu
                140                 145                 150

GAG GAT GTT AAA AAG TTG TAC CAC TCA GAA GCC TTC ACT GTC AAC TTC       534
Glu Asp Val Lys Lys Leu Tyr His Ser Glu Ala Phe Thr Val Asn Phe
            155                 160                 165

GGG GAC ACC GAA GAG GCC AAG AAA CAG ATC AAC GAT TAC GTG GAG AAG       582
Gly Asp Thr Glu Glu Ala Lys Lys Gln Ile Asn Asp Tyr Val Glu Lys
        170                 175                 180

GGT ACT CAA GGG AAA ATT GTG GAT TTG GTC AAG GAG CTT GAC AGA GAC       630
Gly Thr Gln Gly Lys Ile Val Asp Leu Val Lys Glu Leu Asp Arg Asp
185                 190                 195

ACA GTT TTT GCT CTG GTG AAT TAC ATC TTC TTT AAA GGC AAA TGG GAG       678
Thr Val Phe Ala Leu Val Asn Tyr Ile Phe Phe Lys Gly Lys Trp Glu
200                 205                 210                 215

AGA CCC TTT GAA GTC AAG GAC ACC GAG GAA GAG GAC TTC CAC GTG GAC       726
Arg Pro Phe Glu Val Lys Asp Thr Glu Glu Glu Asp Phe His Val Asp
                220                 225                 230

CAG GTG ACC ACC GTG AAG GTG CCT ATG ATG AAG CGT TTA GGC ATG TTT       774
Gln Val Thr Thr Val Lys Val Pro Met Met Lys Arg Leu Gly Met Phe
            235                 240                 245
```

```
AAC ATC CAG CAC TGT AAG AAG CTG TCC AGC TGG GTG CTG CTG ATG AAA        822
Asn Ile Gln His Cys Lys Lys Leu Ser Ser Trp Val Leu Leu Met Lys
            250                 255                 260

TAC CTG GGC AAT GCC ACC GCC ATG TTC TTC CTG CCT GAT GAG GGG AAA        870
Tyr Leu Gly Asn Ala Thr Ala Met Phe Phe Leu Pro Asp Glu Gly Lys
265                 270                 275

CTA CAG CAC CTG GAA AAT GAA CTC ACC CAC GAT ATC ATC ACC AAG TTC        918
Leu Gln His Leu Glu Asn Glu Leu Thr His Asp Ile Ile Thr Lys Phe
280                 285                 290                 295

CTG GAA AAT GAA GAC AGA AGG TCT GCC AGC TTA CAT TTA CCC AAA CTG        966
Leu Glu Asn Glu Asp Arg Arg Ser Ala Ser Leu His Leu Pro Lys Leu
                300                 305                 310

TCC ATT ACT GGA ACC TAT GAT CTG AAG AGC GTC CTG GGT CAA CTG GGC       1014
Ser Ile Thr Gly Thr Tyr Asp Leu Lys Ser Val Leu Gly Gln Leu Gly
            315                 320                 325

ATC ACT AAG GTC TTC AGC AAT GGG GCT GAC CTC TCC GGG GTC ACA GAG       1062
Ile Thr Lys Val Phe Ser Asn Gly Ala Asp Leu Ser Gly Val Thr Glu
        330                 335                 340

GAG GCA CCC CTG AAG CTC TCC AAG GCC GTG CAT AAG GCT GTG CTG ACC       1110
Glu Ala Pro Leu Lys Leu Ser Lys Ala Val His Lys Ala Val Leu Thr
    345                 350                 355

ATC GAC GAG AAA GGG ACT GAA GCT GCT GGG GCC ATG TTT TTA GAG GCC       1158
Ile Asp Glu Lys Gly Thr Glu Ala Ala Gly Ala Met Phe Leu Glu Ala
360                 365                 370                 375

ATA CCC ATG TCT ATC CCC CCC GAG GTC AAG TTC AAC AAA CCC TTT GTC       1206
Ile Pro Met Ser Ile Pro Pro Glu Val Lys Phe Asn Lys Pro Phe Val
                380                 385                 390

TTC TTA ATG ATT GAA CAA AAT ACC AAG TCT CCC CTC TTC ATG GGA AAA       1254
Phe Leu Met Ile Glu Gln Asn Thr Lys Ser Pro Leu Phe Met Gly Lys
            395                 400                 405

GTG GTG AAT CCC ACC CAA AAA TAACTGCTCG CTCCTCAACC CCTCCCCTCC          1305
Val Val Asn Pro Thr Gln Lys
        410

ATCCCTGGCC CCCTCCCTGG ATGACATTAA AGAAGGGTTG AGCTGGAAAA A              1356

(2) INFORMATION FOR SEQ ID NO:17:

(i) SEQUENCE CHARACTERISTICS:
        (A) LENGTH: 414 amino acids
        (B) TYPE: amino acid
        (D) TOPOLOGY: linear (ii) MOLECULE TYPE: protein (xi) SEQUENCE DESCRIPTION: SEQ ID NO:17:

Met Pro Ser Ser Val Ser Trp Gly Ile Leu Leu Leu Ala Gly Leu Cys
1               5                   10                  15

Cys Leu Val Pro Val Ser Leu Ala Glu Asp Pro Gln Gly Asp Ala Ala
                20                  25                  30

Gln Lys Thr Asp Thr Ser His His Asp Gln Asp His Pro Thr Phe Asn
            35                  40                  45

Lys Ile Thr Pro Asn Leu Ala Glu Phe Ala Phe Ser Leu Tyr Arg Gln
        50                  55                  60

Leu Ala His Gln Ser Asn Ser Thr Asn Ile Phe Phe Ser Pro Val Ser
65                  70                  75                  80

Ile Ala Thr Ala Phe Ala Met Leu Ser Leu Gly Thr Lys Ala Asp Thr
                85                  90                  95

His Asp Glu Ile Leu Glu Gly Leu Asn Phe Asn Leu Thr Glu Ile Pro
            100                 105                 110
```

```
Glu Pro Gln Ile His Glu Gly Phe Gln Glu Leu Leu Arg Thr Leu Asn
            115                 120                 125

Gln Leu Gln Leu Thr Thr Gly Asn Gly Leu Phe Leu Ser Glu Gly Leu
        130                 135                 140

Lys Leu Val Asp Lys Phe Leu Glu Asp Val Lys Lys Leu Tyr His Ser
145                 150                 155                 160

Glu Ala Phe Thr Val Asn Phe Gly Asp Thr Glu Glu Ala Lys Lys Gln
                165                 170                 175

Ile Asn Asp Tyr Val Glu Lys Gly Thr Gln Gly Lys Ile Val Asp Leu
            180                 185                 190

Val Lys Glu Leu Asp Arg Asp Thr Val Phe Ala Leu Val Asn Tyr Ile
        195                 200                 205

Phe Phe Lys Gly Lys Trp Glu Arg Pro Phe Glu Val Lys Asp Thr Glu
210                 215                 220

Glu Glu Asp Phe His Val Asp Gln Val Thr Thr Val Lys Val Pro Met
225                 230                 235                 240

Met Lys Arg Leu Gly Met Phe Asn Ile Gln His Cys Lys Lys Leu Ser
                245                 250                 255

Ser Trp Val Leu Leu Met Lys Tyr Leu Gly Asn Ala Thr Ala Met Phe
            260                 265                 270

Phe Leu Pro Asp Glu Gly Lys Leu Gln His Leu Glu Asn Glu Leu Thr
        275                 280                 285

His Asp Ile Ile Thr Lys Phe Leu Glu Asn Glu Asp Arg Arg Ser Ala
290                 295                 300

Ser Leu His Leu Pro Lys Leu Ser Ile Thr Gly Thr Tyr Asp Leu Lys
305                 310                 315                 320

Ser Val Leu Gly Gln Leu Gly Ile Thr Lys Val Phe Ser Asn Gly Ala
                325                 330                 335

Asp Leu Ser Gly Val Thr Glu Glu Ala Pro Leu Lys Leu Ser Lys Ala
            340                 345                 350

Val His Lys Ala Val Leu Thr Ile Asp Glu Lys Gly Thr Glu Ala Ala
        355                 360                 365

Gly Ala Met Phe Leu Glu Ala Ile Pro Met Ser Ile Pro Pro Glu Val
370                 375                 380

Lys Phe Asn Lys Pro Phe Val Phe Leu Met Ile Glu Gln Asn Thr Lys
385                 390                 395                 400

Ser Pro Leu Phe Met Gly Lys Val Val Asn Pro Thr Gln Lys
                405                 410
```

(2) INFORMATION FOR SEQ ID NO:18:

(i) SEQUENCE CHARACTERISTICS:
        (A) LENGTH: 1356 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 34..1275
        (C) OTHER INFORMATION: /product= alpha-1-antitrypsin
            variant Portland"
            / standard_name= alpha-1-antitrypsin Portland (xi) SEQUENCE DESCRIPTION: SEQ ID NO:18:

```
GCACCACCAC TGACCTGGGA CAGTGAATCG ACA ATG CCG TCT TCT GTC TCG TGG     54
                                    Met Pro Ser Ser Val Ser Trp
```

-continued

```
                    1                   5
GGC ATC CTC CTG CTG GCA GGC TGC TGC CTG GTC CCT GTC TCC CTG         102
Gly Ile Leu Leu Leu Ala Gly Leu Cys Cys Leu Val Pro Val Ser Leu
        10                  15                  20

GCT GAG GAT CCC CAG GGA GAT GCT GCC CAG AAG ACA GAT ACA TCC CAC     150
Ala Glu Asp Pro Gln Gly Asp Ala Ala Gln Lys Thr Asp Thr Ser His
    25                  30                  35

CAT GAT CAG GAT CAC CCA ACC TTC AAC AAG ATC ACC CCC AAC CTG GCT     198
His Asp Gln Asp His Pro Thr Phe Asn Lys Ile Thr Pro Asn Leu Ala
40                  45                  50                  55

GAG TTC GCC TTC AGC CTA TAC CGC CAG CTG GCA CAC CAG TCC AAC AGC     246
Glu Phe Ala Phe Ser Leu Tyr Arg Gln Leu Ala His Gln Ser Asn Ser
                60                  65                  70

ACC AAT ATC TTC TTC TCC CCA GTG AGC ATC GCT ACA GCC TTT GCA ATG     294
Thr Asn Ile Phe Phe Ser Pro Val Ser Ile Ala Thr Ala Phe Ala Met
            75                  80                  85

CTC TCC CTG GGG ACC AAG GCT GAC ACT CAC GAT GAA ATC CTG GAG GGC     342
Leu Ser Leu Gly Thr Lys Ala Asp Thr His Asp Glu Ile Leu Glu Gly
        90                  95                 100

CTG AAT TTC AAC CTC ACG GAG ATT CCG GAG CCT CAG ATC CAT GAA GGC     390
Leu Asn Phe Asn Leu Thr Glu Ile Pro Glu Pro Gln Ile His Glu Gly
    105                 110                 115

TTC CAG GAA CTC CTC CGT ACC CTC AAC CAG CTC CAG CTG ACC ACC GGC     438
Phe Gln Glu Leu Leu Arg Thr Leu Asn Gln Leu Gln Leu Thr Thr Gly
120                 125                 130                 135

AAT GGC CTG TTC CTC AGC GAG GGC CTG AAG CTA GTG GAT AAG TTT TTG     486
Asn Gly Leu Phe Leu Ser Glu Gly Leu Lys Leu Val Asp Lys Phe Leu
                140                 145                 150

GAG GAT GTT AAA AAG TTG TAC CAC TCA GAA GCC TTC ACT GTC AAC TTC     534
Glu Asp Val Lys Lys Leu Tyr His Ser Glu Ala Phe Thr Val Asn Phe
            155                 160                 165

GGG GAC ACC GAA GAG GCC AAG AAA CAG ATC AAC GAT TAC GTG GAG AAG     582
Gly Asp Thr Glu Glu Ala Lys Lys Gln Ile Asn Asp Tyr Val Glu Lys
        170                 175                 180

GGT ACT CAA GGG AAA ATT GTG GAT TTG GTC AAG GAG CTT GAC AGA GAC     630
Gly Thr Gln Gly Lys Ile Val Asp Leu Val Lys Glu Leu Asp Arg Asp
    185                 190                 195

ACA GTT TTT GCT CTG GTG AAT TAC ATC TTC TTT AAA GGC AAA TGG GAG     678
Thr Val Phe Ala Leu Val Asn Tyr Ile Phe Phe Lys Gly Lys Trp Glu
200                 205                 210                 215

AGA CCC TTT GAA GTC AAG GAC ACC GAG GAA GAG GAC TTC CAC GTG GAC     726
Arg Pro Phe Glu Val Lys Asp Thr Glu Glu Glu Asp Phe His Val Asp
                220                 225                 230

CAG GTG ACC ACC GTG AAG GTG CCT ATG ATG AAG CGT TTA GGC ATG TTT     774
Gln Val Thr Thr Val Lys Val Pro Met Met Lys Arg Leu Gly Met Phe
            235                 240                 245

AAC ATC CAG CAC TGT AAG AAG CTG TCC AGC TGG GTG CTG CTG ATG AAA     822
Asn Ile Gln His Cys Lys Lys Leu Ser Ser Trp Val Leu Leu Met Lys
        250                 255                 260

TAC CTG GGC AAT GCC ACC GCC ATG TTC TTC CTG CCT GAT GAG GGG AAA     870
Tyr Leu Gly Asn Ala Thr Ala Met Phe Phe Leu Pro Asp Glu Gly Lys
    265                 270                 275

CTA CAG CAC CTG GAA AAT GAA CTC ACC CAC GAT ATC ATC ACC AAG TTC     918
Leu Gln His Leu Glu Asn Glu Leu Thr His Asp Ile Ile Thr Lys Phe
280                 285                 290                 295

CTG GAA AAT GAA GAC AGA AGG TCT GCC AGC TTA CAT TTA CCC AAA CTG     966
Leu Glu Asn Glu Asp Arg Arg Ser Ala Ser Leu His Leu Pro Lys Leu
                300                 305                 310

TCC ATT ACT GGA ACC TAT GAT CTG AAG AGC GTC CTG GGT CAA CTG GGC    1014
```

```
Ser Ile Thr Gly Thr Tyr Asp Leu Lys Ser Val Leu Gly Gln Leu Gly
            315                 320                 325

ATC ACT AAG GTC TTC AGC AAT GGG GCT GAC CTC TCC GGG GTC ACA GAG      1062
Ile Thr Lys Val Phe Ser Asn Gly Ala Asp Leu Ser Gly Val Thr Glu
        330                 335                 340

GAG GCA CCC CTG AAG CTC TCC AAG GCC GTG CAT AAG GCT GTG CTG ACC      1110
Glu Ala Pro Leu Lys Leu Ser Lys Ala Val His Lys Ala Val Leu Thr
    345                 350                 355

ATC GAC GAG AAA GGG ACT GAA GCT GCT GGG GCC ATG TTT TTA GAG CGC      1158
Ile Asp Glu Lys Gly Thr Glu Ala Ala Gly Ala Met Phe Leu Glu Arg
360                 365                 370                 375

ATA CCC AGG TCT ATC CCC CCC GAG GTC AAG TTC AAC AAA CCC TTT GTC      1206
Ile Pro Arg Ser Ile Pro Pro Glu Val Lys Phe Asn Lys Pro Phe Val
                380                 385                 390

TTC TTA ATG ATT GAA CAA AAT ACC AAG TCT CCC CTC TTC ATG GGA AAA      1254
Phe Leu Met Ile Glu Gln Asn Thr Lys Ser Pro Leu Phe Met Gly Lys
            395                 400                 405

GTG GTG AAT CCC ACC CAA AAA TAACTGCTCG CTCCTCAACC CCTCCCCTCC         1305
Val Val Asn Pro Thr Gln Lys
        410

ATCCCTGGCC CCCTCCCTGG ATGACATTAA AGAAGGGTTG AGCTGGAAAA A             1356
```

(2) INFORMATION FOR SEQ ID NO:19:

(i) SEQUENCE CHARACTERISTICS:
        (A) LENGTH: 414 amino acids
        (B) TYPE: amino acid
        (D) TOPOLOGY: linear (ii) MOLECULE TYPE: protein (xi) SEQUENCE DESCRIPTION: SEQ ID NO:19:

```
Met Pro Ser Ser Val Ser Trp Gly Ile Leu Leu Leu Ala Gly Leu Cys
 1               5                  10                  15

Cys Leu Val Pro Val Ser Leu Ala Glu Asp Pro Gln Gly Asp Ala Ala
                20                  25                  30

Gln Lys Thr Asp Thr Ser His His Asp Gln Asp His Pro Thr Phe Asn
            35                  40                  45

Lys Ile Thr Pro Asn Leu Ala Glu Phe Ala Phe Ser Leu Tyr Arg Gln
        50                  55                  60

Leu Ala His Gln Ser Asn Ser Thr Asn Ile Phe Phe Ser Pro Val Ser
65                  70                  75                  80

Ile Ala Thr Ala Phe Ala Met Leu Ser Leu Gly Thr Lys Ala Asp Thr
                85                  90                  95

His Asp Glu Ile Leu Glu Gly Leu Asn Phe Asn Leu Thr Glu Ile Pro
            100                 105                 110

Glu Pro Gln Ile His Glu Gly Phe Gln Glu Leu Leu Arg Thr Leu Asn
        115                 120                 125

Gln Leu Gln Leu Thr Thr Gly Asn Gly Leu Phe Leu Ser Glu Gly Leu
    130                 135                 140

Lys Leu Val Asp Lys Phe Leu Glu Asp Val Lys Lys Leu Tyr His Ser
145                 150                 155                 160

Glu Ala Phe Thr Val Asn Phe Gly Asp Thr Glu Glu Ala Lys Lys Gln
                165                 170                 175

Ile Asn Asp Tyr Val Glu Lys Gly Thr Gln Gly Lys Ile Val Asp Leu
            180                 185                 190

Val Lys Glu Leu Asp Arg Asp Thr Val Phe Ala Leu Val Asn Tyr Ile
        195                 200                 205
```

```
Phe Phe Lys Gly Lys Trp Glu Arg Pro Phe Glu Val Lys Asp Thr Glu
        210                 215                 220
Glu Glu Asp Phe His Val Asp Gln Val Thr Thr Val Lys Val Pro Met
225                 230                 235                 240
Met Lys Arg Leu Gly Met Phe Asn Ile Gln His Cys Lys Lys Leu Ser
                245                 250                 255
Ser Trp Val Leu Leu Met Lys Tyr Leu Gly Asn Ala Thr Ala Met Phe
                260                 265                 270
Phe Leu Pro Asp Glu Gly Lys Leu Gln His Leu Glu Asn Glu Leu Thr
                275                 280                 285
His Asp Ile Ile Thr Lys Phe Leu Glu Asn Glu Asp Arg Arg Ser Ala
        290                 295                 300
Ser Leu His Leu Pro Lys Leu Ser Ile Thr Gly Thr Tyr Asp Leu Lys
305                 310                 315                 320
Ser Val Leu Gly Gln Leu Gly Ile Thr Lys Val Phe Ser Asn Gly Ala
                325                 330                 335
Asp Leu Ser Gly Val Thr Glu Glu Ala Pro Leu Lys Leu Ser Lys Ala
                340                 345                 350
Val His Lys Ala Val Leu Thr Ile Asp Glu Lys Gly Thr Glu Ala Ala
        355                 360                 365
Gly Ala Met Phe Leu Glu Arg Ile Pro Arg Ser Ile Pro Pro Glu Val
        370                 375                 380
Lys Phe Asn Lys Pro Phe Val Phe Leu Met Ile Glu Gln Asn Thr Lys
385                 390                 395                 400
Ser Pro Leu Phe Met Gly Lys Val Val Asn Pro Thr Gln Lys
                405                 410

(2) INFORMATION FOR SEQ ID NO:20:

(i) SEQUENCE CHARACTERISTICS:
        (A) LENGTH: 4 amino acids
        (B) TYPE: amino acid
        (D) TOPOLOGY: linear (ii) MOLECULE TYPE: peptide (ix) FEATURE:
        (A) NAME/KEY: Modified site
        (B) LOCATION: 1..4
        (C) OTHER INFORMATION: /label=Modified site
            / note="The amino terminus us derivatized by a
            butoxycarbonyl group, and the carboxyl terminus
            is derivatized by a 4-methylcoumaryl-7-amide group."

(xi) SEQUENCE DESCRIPTION: SEQ ID NO:20:

Arg Val Arg Arg
1

(2) INFORMATION FOR SEQ ID NO:21:

(i) SEQUENCE CHARACTERISTICS:
        (A) LENGTH: 4 amino acids
        (B) TYPE: amino acid
        (D) TOPOLOGY: linear (ii) MOLECULE TYPE: peptide (ix) FEATURE:
        (A) NAME/KEY: Modified site
        (B) LOCATION: 1..4
        (C) OTHER INFORMATION: /label=Modified site
            / note="The amino terminus us derivatized by a
            butoxycarbonyl group, and the carboxyl terminus
```

-continued is derivatized by a para-nitroanilide group."

(xi) SEQUENCE DESCRIPTION: SEQ ID NO:21:

Ala Ala Pro Ala